United States Patent
Hilvert et al.

(10) Patent No.: US 11,925,698 B2
(45) Date of Patent: Mar. 12, 2024

(54) WATER-SOLUBLE FIBROUS POUCH CONTAINING PRILLS FOR HAIR CARE

(71) Applicant: The Procter & Gamble Company, Cincinnati, OH (US)

(72) Inventors: Jennifer Elaine Hilvert, Cincinnati, OH (US); Mark William Hamersky, Hamilton, OH (US); Gemma Zoe Braganza, Singapore (SG); Eric Paul Granberg, Cincinnati, OH (US); Jorge Max Sunkel, West Chester, OH (US); Junichi Yokogi, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/389,758

(22) Filed: Jul. 30, 2021

(65) Prior Publication Data

US 2022/0031579 A1 Feb. 3, 2022

Related U.S. Application Data

(60) Provisional application No. 63/059,365, filed on Jul. 31, 2020.

(51) Int. Cl.
| | |
|---|---|
| *A61K 8/02* | (2006.01) |
| *A61K 8/27* | (2006.01) |
| *A61K 8/44* | (2006.01) |
| *A61K 8/49* | (2006.01) |

(Continued)

(52) U.S. Cl.
CPC .......... *A61K 8/0216* (2013.01); *A61K 8/0208* (2013.01); *A61K 8/27* (2013.01); *A61K 8/44* (2013.01); *A61K 8/4926* (2013.01); *A61Q 5/006* (2013.01); *A61Q 5/12* (2013.01); *A61K 2800/30* (2013.01); *A61K 2800/33* (2013.01)

(58) Field of Classification Search
None
See application file for complete search history.

(56) References Cited

U.S. PATENT DOCUMENTS

| | | | |
|---|---|---|---|
| 1,421,350 A | 6/1922 | Powell | |
| 2,356,168 A | 8/1944 | Mabley | |
| 2,396,278 A | 3/1946 | Otto | |

(Continued)

FOREIGN PATENT DOCUMENTS

| | | |
|---|---|---|
| AU | 2004202461 B2 | 11/2007 |
| CA | 2300638 A1 | 8/2000 |

(Continued)

OTHER PUBLICATIONS

"Green Chemistry", Huazhong University of Science and Technology Press, published on Jun. 30, 2008, pp. 6.

(Continued)

*Primary Examiner* — Nicole P Babson
(74) *Attorney, Agent, or Firm* — Alexandra S. Anoff

(57) ABSTRACT

A water-soluble pouch for hair care with a water-soluble fibrous facing sheet and a water-soluble backing sheet. The facing sheet and backing sheet are joined by a seal along at least a portion of the perimeter. A plurality of hair conditioner prills are disposed within the internal volume. The prills can include both cationic surfactant and fatty alcohol and can have a melting point greater than 45°.

18 Claims, 4 Drawing Sheets

(51) Int. Cl.
*A61Q 5/00* (2006.01)
*A61Q 5/12* (2006.01)

(56) References Cited

U.S. PATENT DOCUMENTS

| | | |
|---|---|---|
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,613,185 A | 10/1952 | Marshall |
| 2,648,635 A | 8/1953 | Jacques et al. |
| 2,658,072 A | 11/1953 | Milton |
| 2,694,668 A | 11/1954 | Fricke |
| 2,809,971 A | 10/1957 | Jack et al. |
| 3,152,046 A | 10/1964 | Maria |
| 3,157,611 A | 11/1964 | Lindemann |
| 3,236,733 A | 2/1966 | Karsten et al. |
| 3,293,718 A | 12/1966 | Melvin |
| 3,321,425 A | 5/1967 | Karl-ludwig et al. |
| 3,332,880 A | 7/1967 | Adriaan et al. |
| 3,426,440 A | 2/1969 | Shen et al. |
| 3,428,478 A | 2/1969 | Donaldson et al. |
| 3,452,382 A | 7/1969 | Kazdan |
| 3,463,308 A | 8/1969 | Deneke |
| 3,489,688 A | 1/1970 | Pospischil |
| 3,570,122 A | 3/1971 | Willimas |
| 3,589,007 A | 6/1971 | Walton |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,859,125 A | 1/1975 | Miller |
| 3,875,300 A | 4/1975 | Homm et al. |
| 3,904,543 A | 9/1975 | Knighten |
| 3,929,678 A | 12/1975 | Laughlin |
| 3,943,949 A | 3/1976 | Ashton et al. |
| 3,954,113 A | 5/1976 | Bohrer et al. |
| 3,957,921 A | 5/1976 | Iwahashi et al. |
| 3,967,921 A | 7/1976 | Haberli et al. |
| 4,020,156 A | 4/1977 | Murray et al. |
| 4,024,078 A | 5/1977 | Gilbert et al. |
| 4,033,365 A | 7/1977 | Klepak et al. |
| 4,051,081 A | 9/1977 | Jabs et al. |
| 4,089,945 A | 5/1978 | Brinkman et al. |
| 4,149,551 A | 4/1979 | Benjamin et al. |
| 4,180,558 A | 12/1979 | Franklin |
| 4,185,125 A | 1/1980 | Kimura et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,286,016 A | 8/1981 | Dimond |
| 4,287,219 A | 9/1981 | Fabre |
| 4,315,965 A | 2/1982 | Mason |
| 4,323,525 A | 4/1982 | Bornat |
| 4,323,683 A | 4/1982 | Bolich, Jr. et al. |
| 4,340,583 A | 7/1982 | Wason |
| 4,342,813 A | 8/1982 | Erickson |
| 4,345,080 A | 8/1982 | Bolich, Jr. |
| 4,349,531 A | 9/1982 | Mlodozeniec |
| D266,829 S | 11/1982 | Yoshizawa et al. |
| 4,377,615 A | 3/1983 | Suzuki |
| 4,379,753 A | 4/1983 | Bolich, Jr. |
| 4,381,919 A | 5/1983 | Jacquet et al. |
| 4,415,617 A | 11/1983 | D'Elia |
| 4,422,853 A | 12/1983 | Jacquet et al. |
| 4,448,699 A | 5/1984 | Barrat et al. |
| 4,470,982 A | 9/1984 | Winkler |
| 4,507,280 A | 3/1985 | Pohl et al. |
| 4,529,586 A | 7/1985 | De Marco et al. |
| 4,536,361 A | 8/1985 | Torobin |
| 4,565,647 A | 1/1986 | Llenado |
| D286,450 S | 10/1986 | Tovey |
| 4,635,351 A | 1/1987 | Koch et al. |
| 4,637,859 A | 1/1987 | Trokhan |
| 4,639,390 A | 1/1987 | Shoji |
| 4,663,158 A | 5/1987 | Wolfram et al. |
| 4,683,001 A | 7/1987 | Floyd |
| 4,710,374 A | 12/1987 | Grollier et al. |
| 4,723,362 A | 2/1988 | Boerger |
| 4,727,410 A | 2/1988 | Higgins, III |
| 4,822,613 A | 4/1989 | Rodero |
| 4,885,107 A | 12/1989 | Wetzel |
| 4,892,758 A | 1/1990 | Serbiak |
| 4,923,660 A | 5/1990 | Willenberg |
| 4,976,953 A | 12/1990 | Orr et al. |
| 4,990,280 A | 2/1991 | Thorengaard |
| 5,034,421 A | 7/1991 | Fuisz |
| 5,041,252 A | 8/1991 | Fujii |
| 5,052,296 A | 10/1991 | Shiba |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,102,129 A | 4/1992 | Roberts |
| 5,104,646 A | 4/1992 | Bolich, Jr. |
| 5,106,609 A | 4/1992 | Bolich, Jr. |
| 5,110,678 A | 5/1992 | Narukawa |
| 5,112,515 A | 5/1992 | Buxton et al. |
| 5,120,888 A | 6/1992 | Nohr |
| 5,135,804 A | 8/1992 | Harpell |
| 5,158,810 A | 10/1992 | Oishi |
| 5,166,276 A | 11/1992 | Hayama et al. |
| D334,420 S | 3/1993 | Copeland et al. |
| 5,208,104 A | 5/1993 | Ueda |
| 5,220,033 A | 6/1993 | Kamei et al. |
| 5,230,853 A | 7/1993 | Colegrove |
| 5,261,426 A | 11/1993 | Kellett et al. |
| 5,280,079 A | 1/1994 | Allen et al. |
| RE34,584 E | 4/1994 | Grote et al. |
| 5,342,335 A | 8/1994 | Rhim |
| D351,345 S | 10/1994 | Geho |
| 5,362,532 A | 11/1994 | Famili |
| 5,364,627 A | 11/1994 | Song |
| 5,387,147 A | 2/1995 | Ohshima |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee et al. |
| 5,429,628 A | 7/1995 | Trinh et al. |
| 5,429,874 A | 7/1995 | Vanputte |
| 5,444,113 A | 8/1995 | Sinclair et al. |
| 5,446,079 A | 8/1995 | Buchanan et al. |
| 5,455,114 A | 10/1995 | Ohmory |
| 5,457,895 A | 10/1995 | Thompson et al. |
| 5,458,433 A | 10/1995 | Stastny |
| 5,470,424 A | 11/1995 | Isaac |
| 5,470,492 A | 11/1995 | Childs et al. |
| 5,470,653 A | 11/1995 | Honeycutt |
| 5,476,597 A | 12/1995 | Sakata et al. |
| 5,486,418 A | 1/1996 | Ohmory |
| 5,501,238 A | 3/1996 | Borstel et al. |
| 5,518,730 A | 5/1996 | Fuisz |
| 5,520,924 A | 5/1996 | Chapman |
| 5,533,636 A | 7/1996 | Reiker |
| 5,538,735 A | 7/1996 | Ahn |
| 5,580,481 A | 12/1996 | Sakata et al. |
| 5,582,786 A | 12/1996 | Brunskill et al. |
| 5,585,059 A | 12/1996 | Kobayashi |
| D378,180 S | 2/1997 | Hayes et al. |
| 5,651,987 A | 7/1997 | Fuisz |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,691,015 A | 11/1997 | Tsukamoto |
| 5,705,183 A | 1/1998 | Phillips |
| 5,716,692 A | 2/1998 | Warner |

(56) References Cited

U.S. PATENT DOCUMENTS

| | | |
|---|---|---|
| 5,717,026 A | 2/1998 | Ikimine |
| 5,735,812 A | 4/1998 | Hardy |
| 5,750,122 A | 5/1998 | Evans |
| 5,756,438 A | 5/1998 | Rau et al. |
| 5,780,047 A | 7/1998 | Kamiya et al. |
| 5,780,418 A | 7/1998 | Niinaka |
| D398,847 S | 9/1998 | Wyslotsky et al. |
| D399,260 S | 10/1998 | Thimote |
| 5,827,586 A | 10/1998 | Yamashita |
| 5,840,423 A | 11/1998 | Sano |
| 5,840,675 A | 11/1998 | Yeazell |
| 5,849,378 A | 12/1998 | Gask |
| 5,863,887 A | 1/1999 | Gillette |
| 5,879,493 A | 3/1999 | Johnson |
| D407,640 S | 4/1999 | Crapser et al. |
| D408,223 S | 4/1999 | Henry |
| 5,911,224 A | 6/1999 | Berger |
| 5,914,124 A | 6/1999 | Mahoney |
| 5,925,603 A | 7/1999 | D'Angelo |
| 5,942,179 A | 8/1999 | Tallentire |
| 5,952,286 A | 9/1999 | Puvvada et al. |
| 5,955,419 A | 9/1999 | Barket, Jr. et al. |
| D416,103 S | 11/1999 | Hashmi |
| 5,976,454 A | 11/1999 | Sterzel et al. |
| D418,415 S | 1/2000 | Hayes et al. |
| D418,750 S | 1/2000 | Blin |
| 6,010,719 A | 1/2000 | Remon et al. |
| 6,028,016 A | 2/2000 | Yahiaoui et al. |
| 6,029,808 A | 2/2000 | Peck et al. |
| 6,034,043 A | 3/2000 | Fujiwara et al. |
| 6,037,319 A | 3/2000 | Dickler |
| 6,066,396 A | 5/2000 | Inada |
| 6,074,997 A | 6/2000 | Rau et al. |
| 6,080,346 A | 6/2000 | Jack |
| D427,902 S | 7/2000 | Hayes et al. |
| 6,106,849 A | 8/2000 | Malkan et al. |
| 6,130,193 A | 10/2000 | Gillette |
| 6,175,054 B1 | 1/2001 | Jacques |
| 6,177,391 B1 | 1/2001 | Zafar |
| 6,197,238 B1 | 3/2001 | Wang |
| 6,200,949 B1 | 3/2001 | Reijmer et al. |
| 6,207,274 B1 | 3/2001 | Ferenc |
| D441,869 S | 5/2001 | Bloor et al. |
| D442,353 S | 5/2001 | Macias |
| D442,739 S | 5/2001 | Friesenhahn |
| D443,389 S | 6/2001 | Friesenhahn |
| 6,274,162 B1 | 8/2001 | Steffenino |
| D448,802 S | 10/2001 | Lariviere, Jr. et al. |
| D449,881 S | 10/2001 | Mock, Sr. |
| D450,378 S | 11/2001 | Minakuchi et al. |
| 6,319,510 B1 | 11/2001 | Yates |
| 6,335,312 B1 | 1/2002 | Coffindaffer et al. |
| 6,365,142 B1 | 4/2002 | Tamura |
| 6,382,526 B1 | 5/2002 | Reneker et al. |
| 6,406,797 B1 | 6/2002 | Vanputte |
| 6,417,156 B1 | 7/2002 | Smith et al. |
| 6,420,625 B1 | 7/2002 | Jones |
| 6,426,091 B1 | 7/2002 | Okumura et al. |
| 6,440,926 B1 | 8/2002 | Spadoni et al. |
| D462,900 S | 9/2002 | Yamada et al. |
| 6,448,462 B2 | 9/2002 | Groitzsch |
| 6,458,754 B1 | 10/2002 | Velazquez et al. |
| 6,465,407 B2 | 10/2002 | Hayashi |
| D465,303 S | 11/2002 | Friesenhahn |
| 6,503,521 B1 | 1/2003 | Atis et al. |
| 6,525,034 B2 | 2/2003 | Dalrymple et al. |
| 6,552,123 B1 | 4/2003 | Katayama |
| 6,576,575 B2 | 6/2003 | Griesbach, III et al. |
| 6,608,121 B2 | 8/2003 | Isozaki |
| D479,561 S | 9/2003 | Meyer |
| 6,623,694 B1 | 9/2003 | Ferguson et al. |
| 6,657,004 B2 | 12/2003 | Mizutani |
| D484,749 S | 1/2004 | Garraway |
| 6,699,826 B1 | 3/2004 | Saijo |
| 6,723,160 B2 | 4/2004 | Mackey et al. |
| D489,162 S | 5/2004 | Dings-plooij |
| 6,730,648 B2 | 5/2004 | Gorlin |
| 6,783,852 B2 | 8/2004 | Inada |
| 6,787,512 B1 | 9/2004 | Verrall |
| 6,790,814 B1 | 9/2004 | Marin |
| 6,800,295 B2 | 10/2004 | Fox |
| 6,802,295 B2 | 10/2004 | Bedwell et al. |
| 6,808,375 B2 | 10/2004 | Kloetzer |
| 6,808,598 B1 | 10/2004 | Takeuchi |
| 6,818,606 B1 | 11/2004 | Hanada |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| 6,898,819 B2 | 5/2005 | Tanaka et al. |
| 6,898,921 B2 | 5/2005 | Duffield |
| D509,935 S | 9/2005 | Burt |
| 6,943,200 B1 | 9/2005 | Corrand et al. |
| 6,946,506 B2 | 9/2005 | Bond |
| 6,949,498 B2 | 9/2005 | Murphy |
| 6,956,070 B2 | 10/2005 | Fujiwara |
| 6,977,116 B2 | 12/2005 | Cabell |
| D515,915 S | 2/2006 | Karim |
| 7,015,181 B2 | 3/2006 | Lambino |
| 7,026,049 B2 | 4/2006 | Endo |
| 7,041,369 B1 | 5/2006 | Mackey et al. |
| 7,067,575 B2 | 6/2006 | Kitamura |
| 7,083,047 B2 | 8/2006 | Bone |
| 7,094,744 B1 | 8/2006 | Kobayashi |
| 7,115,551 B2 | 10/2006 | Hasenoehrl |
| 7,125,828 B2 | 10/2006 | Catlin |
| 7,169,740 B2 | 1/2007 | Sommerville-roberts |
| 7,172,765 B2 | 2/2007 | Chu et al. |
| 7,196,026 B2 | 3/2007 | Di Luccio et al. |
| RE39,557 E | 4/2007 | Moe |
| 7,208,460 B2 | 4/2007 | Shefer et al. |
| 7,221,900 B2 | 5/2007 | Reade et al. |
| 7,226,899 B2 | 6/2007 | Cole |
| D549,051 S | 8/2007 | Nordwall |
| 7,285,520 B2 | 10/2007 | Krzysik |
| 7,291,300 B2 | 11/2007 | Chhabra et al. |
| 7,387,787 B2 | 6/2008 | Fox |
| 7,407,669 B2 | 8/2008 | Leung |
| D576,753 S | 9/2008 | Mukai |
| D577,332 S | 9/2008 | Moore |
| 7,429,273 B2 | 9/2008 | De Dominicis et al. |
| D578,881 S | 10/2008 | Friedland et al. |
| 7,446,084 B2 | 11/2008 | Barthel |
| 7,491,407 B2 | 2/2009 | Pourdeyhimi |
| D588,332 S | 3/2009 | Phelan |
| 7,507,698 B2 | 3/2009 | Franzolin |
| 7,547,737 B2 | 6/2009 | Kochvar |
| 7,563,757 B2 | 7/2009 | Kouvroukoglou |
| 7,704,328 B2 | 4/2010 | Bailey et al. |
| 7,708,840 B2 | 5/2010 | Wiedemann |
| 7,727,946 B2 | 6/2010 | Catalfamo |
| 7,824,588 B2 | 11/2010 | Yang |
| 7,832,552 B2 | 11/2010 | Newman |
| 7,846,462 B2 | 12/2010 | Spadini et al. |
| 7,856,989 B2 | 12/2010 | Karles |
| 7,892,992 B2 | 2/2011 | Kamada et al. |
| 7,901,696 B2 | 3/2011 | Eknoian et al. |
| 7,967,801 B2 | 6/2011 | Hammons |
| D640,921 S | 7/2011 | Caldwell |
| D644,541 S | 9/2011 | Schrader et al. |
| 8,049,061 B2 | 11/2011 | Ehrenreich et al. |
| D651,096 S | 12/2011 | Nakagiri |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. et al. |
| 8,288,332 B2 | 10/2012 | Fossum et al. |
| 8,309,505 B2 | 11/2012 | Fossum et al. |
| 8,349,232 B2 | 1/2013 | Pourdeyhimi |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| 8,367,596 B2 | 2/2013 | Fossum et al. |
| D680,882 S | 4/2013 | Logue |

(56) References Cited

U.S. PATENT DOCUMENTS

| | | |
|---|---|---|
| 8,415,287 B2 | 4/2013 | Glenn, Jr. et al. |
| D682,622 S | 5/2013 | Keys |
| 8,453,653 B2 | 6/2013 | Mishra et al. |
| 8,461,090 B2 | 6/2013 | Glenn, Jr. et al. |
| 8,461,091 B2 | 6/2013 | Glenn, Jr. et al. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,541,081 B1 | 9/2013 | Ranganathan et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. et al. |
| 8,785,361 B2 | 7/2014 | Sivik et al. |
| D712,159 S | 9/2014 | Clerici et al. |
| D712,822 S | 9/2014 | Brusaw et al. |
| 8,962,501 B2 | 2/2015 | Johnson et al. |
| 8,980,816 B2 | 3/2015 | Dreher |
| 9,005,635 B2 | 4/2015 | Darcy et al. |
| 9,062,186 B2 | 6/2015 | Longdon et al. |
| 9,074,305 B2 | 7/2015 | Glenn, Jr. et al. |
| D739,227 S | 9/2015 | Mitchell et al. |
| 9,125,811 B2 | 9/2015 | Tojo et al. |
| 9,139,802 B2 | 9/2015 | Weisman et al. |
| D740,928 S | 10/2015 | Bruining et al. |
| 9,163,205 B2 | 10/2015 | Sivik et al. |
| 9,173,826 B2 | 11/2015 | Schwartz et al. |
| 9,175,250 B2 | 11/2015 | Sivik et al. |
| 9,198,838 B2 | 12/2015 | Glenn, Jr. et al. |
| D748,240 S | 1/2016 | Goode |
| 9,421,153 B2 | 8/2016 | Sivik et al. |
| D769,522 S | 10/2016 | Venet |
| D771,788 S | 11/2016 | Duckwitz |
| 9,480,628 B2 | 11/2016 | Sivik et al. |
| D774,086 S | 12/2016 | Montes et al. |
| D775,198 S | 12/2016 | Montes et al. |
| 9,539,444 B2 | 1/2017 | Kinoshita et al. |
| 9,545,364 B2 | 1/2017 | Glenn, Jr. et al. |
| D778,026 S | 2/2017 | Roetheli |
| D793,025 S | 8/2017 | Slusarczyk et al. |
| D797,551 S | 9/2017 | Chatterton et al. |
| D798,143 S | 9/2017 | Chatterton |
| D808,583 S | 1/2018 | Zietek |
| 9,902,077 B2 | 2/2018 | Park et al. |
| D811,922 S | 3/2018 | Lefave |
| D811,935 S | 3/2018 | Hughes |
| D819,836 S | 6/2018 | Noël |
| 10,045,915 B2 | 8/2018 | Glenn, Jr. et al. |
| D848,102 S | 5/2019 | Carlson et al. |
| D850,041 S | 5/2019 | Endle |
| 10,294,586 B2 | 5/2019 | Sivik et al. |
| D851,344 S | 6/2019 | Carlson et al. |
| D857,156 S | 8/2019 | Hani |
| D857,242 S | 8/2019 | Darrow et al. |
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton et al. |
| D866,105 S | 11/2019 | Carlson et al. |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| 10,646,413 B2 | 5/2020 | Sivik et al. |
| 10,694,917 B2 | 6/2020 | Dreher et al. |
| D901,115 S | 11/2020 | Carlson et al. |
| D903,152 S | 11/2020 | Chao |
| 10,821,056 B2 | 11/2020 | Swartz et al. |
| D906,802 S | 1/2021 | Chi |
| 10,894,005 B2 | 1/2021 | Sivik et al. |
| D910,434 S | 2/2021 | Tan et al. |
| D910,457 S | 2/2021 | Lee |
| D921,166 S | 6/2021 | Meyers |
| D933,095 S | 10/2021 | Heiner et al. |
| 11,351,094 B2 | 6/2022 | Hamersky et al. |
| 11,395,789 B2 | 7/2022 | Pratt et al. |
| 11,419,808 B2 | 8/2022 | Hilvert et al. |
| 11,679,066 B2 | 6/2023 | Song et al. |
| 2001/0037851 A1 | 11/2001 | Mortellite |
| 2002/0018906 A1 | 2/2002 | Clark |
| 2002/0044968 A1 | 4/2002 | van Lengerich |
| 2002/0064510 A1 | 5/2002 | Dalrymple et al. |
| 2002/0077264 A1 | 6/2002 | Roberts et al. |
| 2002/0081732 A1 | 6/2002 | Bowlin et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0161088 A1 | 10/2002 | Kochvar |
| 2002/0169092 A1 | 11/2002 | Alexandre et al. |
| 2002/0173213 A1 | 11/2002 | Chu |
| 2002/0175449 A1 | 11/2002 | Chu et al. |
| 2002/0176827 A1 | 11/2002 | Rajaiah |
| 2002/0177621 A1 | 11/2002 | Hanada et al. |
| 2002/0187181 A1 | 12/2002 | Godbey et al. |
| 2003/0013369 A1 | 1/2003 | Soane et al. |
| 2003/0017208 A1 | 1/2003 | Ignatious |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0045446 A1 | 3/2003 | Dihora |
| 2003/0054966 A1 | 3/2003 | Bone et al. |
| 2003/0069154 A1 | 4/2003 | Hsu et al. |
| 2003/0080150 A1 | 5/2003 | Cowan et al. |
| 2003/0099691 A1 | 5/2003 | Lydzinski et al. |
| 2003/0099692 A1 | 5/2003 | Lydzinski et al. |
| 2003/0114332 A1 | 6/2003 | Ramcharan et al. |
| 2003/0141662 A1 | 7/2003 | Kost et al. |
| 2003/0166489 A1 | 9/2003 | Van Asten et al. |
| 2003/0166495 A1 | 9/2003 | Wang |
| 2003/0180242 A1 | 9/2003 | Eccard et al. |
| 2003/0185872 A1 | 10/2003 | Kochinke |
| 2003/0186826 A1 | 10/2003 | Eccard et al. |
| 2003/0194416 A1 | 10/2003 | Shefer |
| 2003/0199412 A1 | 10/2003 | Gupta |
| 2003/0207776 A1 | 11/2003 | Shefer et al. |
| 2003/0209166 A1 | 11/2003 | Vanmaele et al. |
| 2003/0215522 A1 | 11/2003 | Johnson et al. |
| 2003/0216098 A1 | 11/2003 | Carlyle |
| 2003/0224959 A1 | 12/2003 | Smith |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott et al. |
| 2004/0053808 A1 | 3/2004 | Raehse et al. |
| 2004/0059055 A1 | 3/2004 | Inada et al. |
| 2004/0071742 A1 | 4/2004 | Popplewell |
| 2004/0071755 A1 | 4/2004 | Fox |
| 2004/0082239 A1 | 4/2004 | Di Luccio et al. |
| 2004/0092635 A1 | 5/2004 | Kitamura |
| 2004/0108615 A1 | 6/2004 | Foley |
| 2004/0110656 A1 | 6/2004 | Casey et al. |
| 2004/0116018 A1 | 6/2004 | Fenwick et al. |
| 2004/0116539 A1 | 6/2004 | Biercevicz et al. |
| 2004/0118852 A1 | 6/2004 | Barmore et al. |
| 2004/0126585 A1 | 7/2004 | Kerins et al. |
| 2004/0167256 A1 | 8/2004 | Verrall |
| 2004/0170836 A1 | 9/2004 | Bond |
| 2004/0175404 A1 | 9/2004 | Shefer |
| 2004/0180597 A1 | 9/2004 | Kamada |
| 2004/0202632 A1 | 10/2004 | Gott et al. |
| 2004/0204543 A1 | 10/2004 | Yang |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2004/0253434 A1 | 12/2004 | Patel |
| 2004/0254086 A1 | 12/2004 | Hedges et al. |
| 2004/0266300 A1 | 12/2004 | Isele et al. |
| 2005/0003048 A1 | 1/2005 | Pearce |
| 2005/0003991 A1 | 1/2005 | Macquarrie |

(56) References Cited

U.S. PATENT DOCUMENTS

| | | |
|---|---|---|
| 2005/0008776 A1 | 1/2005 | Chhabra |
| 2005/0010010 A1 | 1/2005 | Kitamura |
| 2005/0069575 A1 | 3/2005 | Fox |
| 2005/0118237 A1 | 6/2005 | Krzysik et al. |
| 2005/0136112 A1 | 6/2005 | Gonzales |
| 2005/0136772 A1 | 6/2005 | Chen et al. |
| 2005/0136780 A1 | 6/2005 | Clark et al. |
| 2005/0137115 A1 | 6/2005 | Cole et al. |
| 2005/0137272 A1 | 6/2005 | Gaserod |
| 2005/0159730 A1 | 7/2005 | Kathrani et al. |
| 2005/0180962 A1 | 8/2005 | Raz et al. |
| 2005/0186256 A1 | 8/2005 | Dihel |
| 2005/0202992 A1 | 9/2005 | Grandio et al. |
| 2005/0209574 A1 | 9/2005 | Boehringer |
| 2005/0220745 A1 | 10/2005 | Lu |
| 2005/0232954 A1 | 10/2005 | Yoshinari et al. |
| 2005/0253297 A1 | 11/2005 | Pedmo et al. |
| 2005/0267005 A1 | 12/2005 | Dasque et al. |
| 2005/0272836 A1 | 12/2005 | Yaginuma et al. |
| 2005/0281757 A1 | 12/2005 | Ibrahim |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0035042 A1 | 2/2006 | Morken |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0083784 A1 | 4/2006 | Ignatious |
| 2006/0089276 A1 | 4/2006 | Klotz |
| 2006/0127458 A1 | 6/2006 | Kiser |
| 2006/0128592 A1 | 6/2006 | Ross et al. |
| 2006/0134412 A1 | 6/2006 | Mackey |
| 2006/0135026 A1 | 6/2006 | Arendt et al. |
| 2006/0159730 A1 | 7/2006 | Simon |
| 2006/0160453 A1 | 7/2006 | Suh |
| 2006/0189772 A1 | 8/2006 | Scheibel |
| 2006/0228319 A1 | 10/2006 | Vona et al. |
| 2006/0254013 A1 | 11/2006 | Konishi |
| 2006/0254014 A1 | 11/2006 | Konishi |
| 2006/0258251 A1 | 11/2006 | Konishi |
| 2006/0264130 A1 | 11/2006 | Karles |
| 2006/0274263 A1 | 12/2006 | Yacktman et al. |
| 2007/0028939 A1 | 2/2007 | Mareri et al. |
| 2007/0054579 A1 | 3/2007 | Baker, Jr. |
| 2007/0098749 A1 | 5/2007 | Eknoian et al. |
| 2007/0099813 A1 | 5/2007 | Luizzi et al. |
| 2007/0110792 A9 | 5/2007 | Simon |
| 2007/0128256 A1 | 6/2007 | Aubrun-sonneville |
| 2007/0134304 A1 | 6/2007 | Aubrun-sonneville |
| 2007/0134481 A1 | 6/2007 | Aubrun-sonneville |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2007/0253926 A1 | 11/2007 | Tadrowski |
| 2007/0259170 A1 | 11/2007 | Brown |
| 2007/0259996 A1 | 11/2007 | Vicari |
| 2007/0269651 A1 | 11/2007 | Denome et al. |
| 2007/0298064 A1 | 12/2007 | Koslow |
| 2008/0008906 A1 | 1/2008 | Catalfamo |
| 2008/0019935 A1 | 1/2008 | Khan |
| 2008/0035174 A1 | 2/2008 | Aubrun-sonneville |
| 2008/0083420 A1 | 4/2008 | Glenn et al. |
| 2008/0087293 A1 | 4/2008 | Glenn et al. |
| 2008/0090939 A1 | 4/2008 | Netravali et al. |
| 2008/0095828 A1 | 4/2008 | Privitera et al. |
| 2008/0108748 A1 | 5/2008 | Buckley |
| 2008/0118727 A1 | 5/2008 | Andersen |
| 2008/0131695 A1 | 6/2008 | Aouad et al. |
| 2008/0138492 A1 | 6/2008 | Cingotti |
| 2008/0146481 A1 | 6/2008 | Brown |
| 2008/0149119 A1 | 6/2008 | Shen |
| 2008/0152894 A1 | 6/2008 | Beihoffer et al. |
| 2008/0153730 A1 | 6/2008 | Tsaur et al. |
| 2008/0215023 A1 | 9/2008 | Scavone et al. |
| 2008/0220054 A1 | 9/2008 | Shastri |
| 2008/0226919 A1 | 9/2008 | Hosoda |
| 2008/0242572 A1 | 10/2008 | Icht |
| 2008/0269095 A1 | 10/2008 | Aubrun-sonneville |
| 2008/0276178 A1 | 11/2008 | Fadell et al. |
| 2008/0279905 A1 | 11/2008 | Kawamoto et al. |
| 2008/0292669 A1 | 11/2008 | Deng et al. |
| 2008/0293839 A1 | 11/2008 | Stobby |
| 2009/0004254 A1 | 1/2009 | Maibach |
| 2009/0041820 A1 | 2/2009 | Wu et al. |
| 2009/0054860 A1 | 2/2009 | Young et al. |
| 2009/0061225 A1 | 3/2009 | Bailey et al. |
| 2009/0061496 A1 | 3/2009 | Kuhn |
| 2009/0061719 A1 | 3/2009 | Shibutani |
| 2009/0144913 A1 | 6/2009 | Yu et al. |
| 2009/0155326 A1 | 6/2009 | Mack |
| 2009/0155383 A1 | 6/2009 | Kitko et al. |
| 2009/0181587 A1 | 7/2009 | Kang |
| 2009/0197787 A1 | 8/2009 | Venet et al. |
| 2009/0232873 A1 | 9/2009 | Glenn, Jr. et al. |
| 2009/0247036 A1 | 10/2009 | Shi et al. |
| 2009/0249558 A1 | 10/2009 | Fileccia |
| 2009/0258099 A1 | 10/2009 | Brown et al. |
| 2009/0263342 A1 | 10/2009 | Glenn, Jr. et al. |
| 2009/0285718 A1 | 11/2009 | Privitera |
| 2009/0286437 A1 | 11/2009 | Cunningham et al. |
| 2009/0291282 A1 | 11/2009 | Kitamura et al. |
| 2009/0293281 A1 | 12/2009 | Bruno |
| 2009/0312220 A1 | 12/2009 | Boutoille |
| 2010/0018641 A1 | 1/2010 | Branham |
| 2010/0021517 A1 | 1/2010 | Ahlers |
| 2010/0098745 A1 | 4/2010 | Staab |
| 2010/0105821 A1 | 4/2010 | Verrall |
| 2010/0135921 A1 | 6/2010 | Hughes et al. |
| 2010/0150976 A1 | 6/2010 | Schnitzler et al. |
| 2010/0166854 A1 | 7/2010 | Michniak-kohn |
| 2010/0167971 A1 | 7/2010 | Glenn, Jr. et al. |
| 2010/0173817 A1 | 7/2010 | Glenn, Jr. et al. |
| 2010/0179083 A1 | 7/2010 | Glenn, Jr. et al. |
| 2010/0196440 A1 | 8/2010 | Stark |
| 2010/0266668 A1 | 10/2010 | Coffee |
| 2010/0279905 A1 | 11/2010 | Glenn, Jr. |
| 2010/0285101 A1 | 11/2010 | Moore |
| 2010/0286011 A1 | 11/2010 | Glenn, Jr. et al. |
| 2010/0291165 A1 | 11/2010 | Glenn, Jr. et al. |
| 2010/0298188 A1 | 11/2010 | Glenn, Jr. et al. |
| 2011/0014252 A1 | 1/2011 | Sagel et al. |
| 2011/0023240 A1 | 2/2011 | Fossum |
| 2011/0027328 A1 | 2/2011 | Baig et al. |
| 2011/0028373 A1 | 2/2011 | Fossum et al. |
| 2011/0028374 A1 | 2/2011 | Fossum et al. |
| 2011/0033509 A1 | 2/2011 | Simon |
| 2011/0045041 A1 | 2/2011 | Golubovic-liakopoulos et al. |
| 2011/0123596 A1 | 5/2011 | Baecker et al. |
| 2011/0129510 A1 | 6/2011 | Liebmann |
| 2011/0136719 A1 | 6/2011 | Jalbert |
| 2011/0159267 A1 | 6/2011 | Lee |
| 2011/0165110 A1 | 7/2011 | Kinoshita et al. |
| 2011/0182956 A1 | 7/2011 | Glenn, Jr. et al. |
| 2011/0189246 A1 | 8/2011 | Glenn, Jr. et al. |
| 2011/0189247 A1 | 8/2011 | Glenn, Jr. et al. |
| 2011/0195098 A1 | 8/2011 | Glenn, Jr. et al. |
| 2011/0223381 A1 | 9/2011 | Sauter |
| 2011/0230112 A1 | 9/2011 | Rose |
| 2011/0250256 A1 | 10/2011 | Hyun-oh et al. |
| 2011/0287687 A1 | 11/2011 | Kramer et al. |
| 2011/0301070 A1 | 12/2011 | Ochomogo |
| 2012/0021026 A1 | 1/2012 | Glenn, Jr. |
| 2012/0027838 A1 | 2/2012 | Gordon et al. |
| 2012/0048769 A1 | 3/2012 | Sivik |
| 2012/0052036 A1 | 3/2012 | Glenn, Jr. |
| 2012/0052037 A1 | 3/2012 | Sivik et al. |
| 2012/0053103 A1 | 3/2012 | Sivik |
| 2012/0053108 A1 | 3/2012 | Glenn, Jr. |
| 2012/0058100 A1 | 3/2012 | Shastri et al. |
| 2012/0058166 A1 | 3/2012 | Glenn, Jr. |
| 2012/0082037 A1 | 4/2012 | Wang |
| 2012/0107534 A1 | 5/2012 | Wnuk et al. |
| 2012/0172831 A1 | 7/2012 | Darcy |

(56) References Cited

U.S. PATENT DOCUMENTS

| | | |
|---|---|---|
| 2012/0215148 A1 | 8/2012 | Ewert |
| 2012/0237576 A1 | 9/2012 | Gordon |
| 2012/0270029 A1 | 10/2012 | Glenn, Jr. et al. |
| 2012/0288693 A1 | 11/2012 | Stanley et al. |
| 2012/0294823 A1 | 11/2012 | Aramwit |
| 2012/0321580 A1 | 12/2012 | Glenn, Jr. |
| 2013/0052277 A1 | 2/2013 | Weiss et al. |
| 2013/0142852 A1 | 6/2013 | Tojo et al. |
| 2013/0171421 A1 | 7/2013 | Weisman |
| 2013/0230482 A1 | 9/2013 | Saguchi et al. |
| 2013/0236520 A1 | 9/2013 | Popovsky et al. |
| 2013/0280979 A1 | 10/2013 | Mckee |
| 2013/0303419 A1 | 11/2013 | Glenn, Jr. et al. |
| 2014/0017402 A1 | 1/2014 | Kleinwaechter et al. |
| 2014/0039114 A1 | 2/2014 | Hagihara et al. |
| 2014/0105946 A1 | 4/2014 | Glenn, Jr. et al. |
| 2014/0127145 A1 | 5/2014 | Deckner |
| 2014/0128345 A1 | 5/2014 | Woodrow et al. |
| 2014/0265007 A1 | 9/2014 | Bruning et al. |
| 2014/0271744 A1 | 9/2014 | Glenn, Jr. et al. |
| 2014/0271745 A1 | 9/2014 | Glenn, Jr. et al. |
| 2014/0287973 A1 | 9/2014 | Sivik |
| 2014/0329428 A1 | 11/2014 | Glenn, Jr. et al. |
| 2015/0071572 A1* | 3/2015 | Dreher .................. B31B 70/74 383/105 |
| 2015/0102307 A1 | 4/2015 | Tajima et al. |
| 2015/0297494 A1 | 10/2015 | Mao et al. |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0008235 A1 | 1/2016 | Sivik et al. |
| 2016/0010041 A1 | 1/2016 | Sivik et al. |
| 2016/0101026 A1 | 4/2016 | Pratt et al. |
| 2016/0101204 A1 | 4/2016 | Lynch et al. |
| 2016/0143827 A1 | 5/2016 | Castan Barberan et al. |
| 2016/0250109 A1 | 9/2016 | Dreher et al. |
| 2016/0324741 A1 | 11/2016 | Baig |
| 2016/0367104 A1 | 12/2016 | Dreher et al. |
| 2017/0121641 A1 | 5/2017 | Smith |
| 2017/0335080 A1 | 11/2017 | Mao et al. |
| 2018/0104177 A1 | 4/2018 | Constantine et al. |
| 2018/0110710 A1 | 4/2018 | Zhao et al. |
| 2018/0140469 A1 | 5/2018 | Kane et al. |
| 2018/0163325 A1 | 6/2018 | Glenn, Jr. et al. |
| 2018/0258555 A1 | 9/2018 | Glenn, Jr. |
| 2018/0311135 A1 | 11/2018 | Chang et al. |
| 2018/0333339 A1 | 11/2018 | Hamersky |
| 2018/0334644 A1 | 11/2018 | Hamersky et al. |
| 2018/0338890 A1 | 11/2018 | Glenn, Jr. |
| 2019/0015875 A1 | 1/2019 | Gardner, Jr. et al. |
| 2019/0282457 A1 | 9/2019 | Pratt et al. |
| 2019/0282461 A1 | 9/2019 | Glassmeyer et al. |
| 2019/0350819 A1 | 11/2019 | Hamersky |
| 2020/0071851 A1 | 3/2020 | Glenn, Jr. et al. |
| 2020/0093710 A1 | 3/2020 | Hamersky et al. |
| 2020/0214946 A1 | 7/2020 | Chan et al. |
| 2020/0261326 A1 | 8/2020 | Sivik et al. |
| 2020/0275818 A1 | 9/2020 | Dreher et al. |
| 2020/0308360 A1 | 10/2020 | Mao et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |
| 2021/0121373 A1 | 4/2021 | Tan et al. |
| 2021/0128417 A1 | 5/2021 | Sivik et al. |
| 2021/0137798 A1 | 5/2021 | Sivik et al. |
| 2021/0147763 A1 | 5/2021 | Tan et al. |
| 2021/0189602 A1 | 6/2021 | Glenn, Jr. et al. |
| 2021/0322290 A1 | 10/2021 | Lynch et al. |
| 2021/0401677 A1 | 12/2021 | Song |
| 2022/0054365 A1 | 2/2022 | Xu et al. |
| 2022/0257476 A1 | 8/2022 | Hamersky et al. |
| 2022/0323309 A1 | 10/2022 | Pratt et al. |
| 2023/0190588 A1 | 6/2023 | Song |

FOREIGN PATENT DOCUMENTS

| | | |
|---|---|---|
| CA | 2524099 A1 | 4/2006 |
| CA | 2695068 A1 | 9/2010 |
| CA | 166297 | 5/2018 |
| CA | 169627 S | 5/2018 |
| CN | 1138091 | 12/1996 |
| CN | 1219388 | 6/1999 |
| CN | 1268558 | 10/2000 |
| CN | 1357613 A | 7/2002 |
| CN | 1454231 A | 11/2003 |
| CN | 1530431 A | 9/2004 |
| CN | 1583991 A | 2/2005 |
| CN | 1726074 A | 1/2006 |
| CN | 3648760 | 5/2007 |
| CN | 101161877 A | 4/2008 |
| CN | 101280467 A | 10/2008 |
| CN | 101424009 A | 5/2009 |
| CN | 101538745 A | 9/2009 |
| CN | 301666535 | 9/2011 |
| CN | 103735428 A | 4/2014 |
| CN | 304115833 | 4/2017 |
| CN | 106726634 A | 5/2017 |
| CN | 106728634 A | 5/2017 |
| CN | 106916659 A | 7/2017 |
| CN | 304537587 | 3/2018 |
| DE | 19607851 A1 | 9/1997 |
| DE | 10331767 A1 | 2/2005 |
| DE | 102007011606 A1 | 9/2008 |
| EP | 0392608 A2 | 10/1990 |
| EP | 609808 A1 | 8/1994 |
| EP | 0858828 A1 | 8/1998 |
| EP | 0948960 A2 | 10/1999 |
| EP | 1048722 A1 | 11/2000 |
| EP | 1160311 A2 | 12/2001 |
| EP | 1214879 A2 | 6/2002 |
| EP | 1227152 A1 | 7/2002 |
| EP | 1275368 A1 | 1/2003 |
| EP | 1306425 A2 | 5/2003 |
| EP | 1217987 B1 | 12/2004 |
| EP | 1574561 A1 | 9/2005 |
| EP | 1375377 B1 | 10/2005 |
| EP | 1614790 A1 | 1/2006 |
| EP | 1409628 B1 | 2/2006 |
| EP | 1512701 B1 | 6/2006 |
| EP | 1887036 A2 | 2/2008 |
| EP | 1888036 | 2/2008 |
| EP | 1958532 A2 | 8/2008 |
| EP | 2085434 A1 | 8/2009 |
| EP | 1436376 B1 | 4/2010 |
| EP | 2226379 A1 | 9/2010 |
| EP | 1317916 B1 | 10/2010 |
| EP | 2246031 A1 | 11/2010 |
| EP | 1948771 B1 | 12/2010 |
| EP | 2319965 A1 | 5/2011 |
| EP | 2363432 A1 | 9/2011 |
| EP | 2363517 A1 | 9/2011 |
| EP | 2395142 A1 | 12/2011 |
| FR | 2871685 A1 | 12/2005 |
| FR | 2886845 A1 | 12/2006 |
| GB | 2107579 A | 5/1983 |
| GB | 2235204 A | 2/1991 |
| GB | 2355008 A | 4/2001 |
| GB | 2375542 A | 11/2002 |
| GB | 2378407 A | 2/2003 |
| GB | 2449418 A | 11/2008 |
| HU | 221299 B1 | 9/2002 |
| IN | 20150354411 | 5/2017 |
| JP | S4912158 A | 2/1974 |
| JP | 58021608 | 2/1983 |
| JP | S58216109 A | 12/1983 |
| JP | S59163458 A | 9/1984 |
| JP | S6272609 A | 4/1987 |
| JP | S6272610 A | 4/1987 |

(56) References Cited

FOREIGN PATENT DOCUMENTS

| | | |
|---|---|---|
| JP | S6281432 A | 4/1987 |
| JP | S6281462 A | 4/1987 |
| JP | 62156348 | 7/1987 |
| JP | S6346251 A | 2/1988 |
| JP | S63156715 A | 6/1988 |
| JP | H01172319 A | 7/1989 |
| JP | H01229805 A | 9/1989 |
| JP | H01313418 A | 12/1989 |
| JP | H0243268 A | 2/1990 |
| JP | H0275650 A | 3/1990 |
| JP | H02280771 A | 11/1990 |
| JP | 3040879 A | 2/1991 |
| JP | 3101618 A | 4/1991 |
| JP | H05344873 A | 12/1993 |
| JP | H0617083 A | 1/1994 |
| JP | H06116568 A | 4/1994 |
| JP | 0753349 | 2/1995 |
| JP | H0789852 A | 4/1995 |
| JP | H07173724 A | 7/1995 |
| JP | H08325133 A | 12/1996 |
| JP | H09216809 A | 8/1997 |
| JP | H09216909 A | 8/1997 |
| JP | 09279457 | 10/1997 |
| JP | 10008364 A | 1/1998 |
| JP | H101824 A | 1/1998 |
| JP | 10158700 A | 6/1998 |
| JP | H10251371 A | 9/1998 |
| JP | H10251952 A | 9/1998 |
| JP | H10512929 A | 12/1998 |
| JP | H11505569 A | 5/1999 |
| JP | H11513053 A | 11/1999 |
| JP | 2000053998 A | 2/2000 |
| JP | 2000169896 A | 6/2000 |
| JP | 2000212828 A | 8/2000 |
| JP | 2000229841 A | 8/2000 |
| JP | 2001302868 A | 10/2001 |
| JP | 2001519376 A | 10/2001 |
| JP | 2002201531 A | 7/2002 |
| JP | 2002226895 A | 8/2002 |
| JP | 2003073700 A | 3/2003 |
| JP | 2003082397 A | 3/2003 |
| JP | 2003532554 A | 11/2003 |
| JP | 2004256799 A | 9/2004 |
| JP | 2004533551 A | 11/2004 |
| JP | 2004345983 A | 12/2004 |
| JP | 2005509734 A | 4/2005 |
| JP | 2005171063 A | 6/2005 |
| JP | 2005534716 A | 11/2005 |
| JP | 2006002337 A | 1/2006 |
| JP | 2006056835 A | 3/2006 |
| JP | 2006511732 A | 4/2006 |
| JP | 3828217 B2 | 7/2006 |
| JP | 2006249029 A | 9/2006 |
| JP | 2007001889 A | 1/2007 |
| JP | 2007091954 A | 4/2007 |
| JP | 2007197365 A | 8/2007 |
| JP | 2007197540 A | 8/2007 |
| JP | 2007528748 A | 10/2007 |
| JP | 2007533763 A | 11/2007 |
| JP | 4128580 B2 | 5/2008 |
| JP | 2008156807 A | 7/2008 |
| JP | 2008525436 A | 7/2008 |
| JP | 2009079329 A | 4/2009 |
| JP | 2009533569 A | 9/2009 |
| JP | 4510221 B2 | 5/2010 |
| JP | 2010100966 A | 5/2010 |
| JP | 2010126856 A | 6/2010 |
| JP | 2013099467 A | 5/2013 |
| JP | 5344873 B2 | 8/2013 |
| JP | 5821609 B2 | 10/2015 |
| JP | 6272610 B2 | 1/2018 |
| KR | 20020003442 A | 1/2002 |
| KR | 20040094520 A | 11/2004 |
| RU | 19735 U1 | 10/2001 |
| RU | 2192451 C2 | 11/2002 |
| RU | 2300196 C2 | 6/2007 |
| RU | 2347557 C2 | 2/2009 |
| TW | 232027 B | 10/1994 |
| WO | 8301943 A1 | 6/1983 |
| WO | 1992006603 A1 | 4/1992 |
| WO | 1994002377 A1 | 2/1994 |
| WO | 9404656 A2 | 3/1994 |
| WO | 9514495 A1 | 6/1995 |
| WO | 9523888 A1 | 9/1995 |
| WO | 9918182 A1 | 4/1999 |
| WO | 9951715 A1 | 10/1999 |
| WO | 9957155 A1 | 11/1999 |
| WO | 2000013680 A2 | 3/2000 |
| WO | 0042992 A2 | 7/2000 |
| WO | 0107194 A1 | 2/2001 |
| WO | 0110421 A1 | 2/2001 |
| WO | 0119948 A1 | 3/2001 |
| WO | 0125322 A1 | 4/2001 |
| WO | 0125393 A1 | 4/2001 |
| WO | 200125322 A1 | 4/2001 |
| WO | 2001024770 A1 | 4/2001 |
| WO | 200154667 A1 | 8/2001 |
| WO | 2001054667 A1 | 8/2001 |
| WO | WO-0183657 A2 * | 11/2001 ............ B65D 25/08 |
| WO | 0238722 A2 | 5/2002 |
| WO | 03044153 A1 | 5/2003 |
| WO | 03060007 A1 | 7/2003 |
| WO | 2004009335 A1 | 1/2004 |
| WO | 2004032859 A2 | 4/2004 |
| WO | 2004041991 A1 | 5/2004 |
| WO | 2004081162 A1 | 9/2004 |
| WO | 2005003423 A1 | 1/2005 |
| WO | 2005068604 A1 | 7/2005 |
| WO | 2005070374 A1 | 8/2005 |
| WO | 2005075547 A1 | 8/2005 |
| WO | 2006106514 A2 | 10/2006 |
| WO | 2007022229 A1 | 2/2007 |
| WO | 2007033598 A1 | 3/2007 |
| WO | 2007089259 A1 | 8/2007 |
| WO | 2007093558 A1 | 8/2007 |
| WO | 2007093619 A1 | 8/2007 |
| WO | 2007102119 A1 | 9/2007 |
| WO | 2008015641 A2 | 2/2008 |
| WO | 2008049242 A1 | 5/2008 |
| WO | 2008104954 A2 | 9/2008 |
| WO | 2008149248 A2 | 12/2008 |
| WO | 2009019571 A2 | 2/2009 |
| WO | 2009022761 A1 | 2/2009 |
| WO | 2007014221 A3 | 4/2009 |
| WO | 2009095891 A1 | 8/2009 |
| WO | 2009103576 A1 | 8/2009 |
| WO | 2009121900 A1 | 10/2009 |
| WO | 2010006708 A1 | 1/2010 |
| WO | 2010015709 A2 | 2/2010 |
| WO | 2010077627 A2 | 7/2010 |
| WO | 2010085569 A1 | 7/2010 |
| WO | 2011153023 A1 | 12/2011 |
| WO | 2012120199 A1 | 9/2012 |
| WO | 2014158472 A1 | 10/2014 |
| WO | 2015034975 A1 | 3/2015 |
| WO | 2015153185 A1 | 10/2015 |
| WO | DM100932 | 4/2018 |
| WO | DM100938 | 4/2018 |
| WO | DM101063 | 5/2018 |
| WO | DM101100 | 5/2018 |
| WO | DM101101 | 5/2018 |
| WO | 2019001940 A1 | 1/2019 |
| WO | 2020192519 A1 | 10/2020 |

OTHER PUBLICATIONS

PCT Search Report and Written Opinion for PCT/US2021/071060 dated Nov. 18, 2021, 12 pages.
Afifi-Effat et al., Polymer Letters, 9: 651-655 (1971).
All Office Actions; U.S. Appl. No. 13/173,639, filed Jun. 30, 2011.
All Office Actions; U.S. Appl. No. 13/229,825, filed Sep. 12, 2011.
All Office Actions; U.S. Appl. No. 14/334,862, filed Jul. 18, 2014.
All Office Actions; U.S. Appl. No. 15/170,125, filed Jun. 1, 2016.

(56) References Cited

OTHER PUBLICATIONS

All Office Actions; U.S. Appl. No. 15/374,486, filed Dec. 9, 2016.
All Office Actions; U.S. Appl. No. 15/978,503, filed May 14, 2018.
All Office Actions; U.S. Appl. No. 16/674,837, filed Nov. 5, 2019.
All Office Actions; U.S. Appl. No. 17/184,712, filed Feb. 25, 2021.
Anonymous "P8136 Poly(vinyl alcohol)" Internet article, [Online] XP002538935, Retrieved from the Internet: URL:hllp/20 NWW.sigmaaldrich.com/catalog/ProductDetail.do?D7=0%N25-SEARCH_CONCAT PNOIBRAND KEY%N4=P8136%7SCIAL%N25=0%QS=ON%F=SPEC retrieved on Jul. 28, 2009, year 2009, 1 pg.
Ashland, Klucel hydroxypropylcelllose, accessed at http://www.ashland.com/Ashland/Static/Documents/ASI/PC_11229_Klucel_HPC.pdf on Apr. 20, 2016.
Briscoe et al. "The effects of hydrogen bonding upon the viscosity of aqueous poly( vinyl alcohol) solutions," from Polymer, 41 (2000), pp. 3851-3860.
Color Keeper [online], [site visited Oct. 18, 2021]. Available from internet, URL: https://shopgemz.com/products/color-keeper?variant=13094595002434&utm_source=google&utm_medium=cpc&utm_campaign=Shopping&gclid=Cj0KCQjw5JSLBhCxARIsAHgO2SdAT7LTehpyxM1qTGtnFETDa1Nuo9_cQSOpPwCmsmmdGA1Y0USekQEaAh0iEALw_wcB (Year: 2021).
Dahiya, A., Karnath, M.G., Hegde, R.R. Melt Blown Technology, Updated Apr. 2004, downloaded from the sitehttp://www.engr.utk.edu/mse/Textiles/Melt%20Blown%20Technology.htm on Dec. 12, 2015.
Definition of Derivative by Merriam Webster Online Dictionary, Year, 2021, 1 Page.
Design of "Detergent tablets" (Design Registration No. 000634142-0003), (No. of Publicly known information: HH18274488), Registered Community Designs Bulletin, published by EUIPO on Jan. 9, 2007, 4 pgs.
Design of "Detergent tablets" (Design Registration No. 000634142-0004), (No. of Publicly known information: HH18274489), Registered Community Designs Bulletin, published by EUIPO on Jan. 9, 2007, 4 pgs.
Dow, UCARE™ Polymer LR-400, Technical Data Sheet, Downloaded in Mar. 2022, 4 pages.
Encyclopedia of Polymer Science and Engineering, vol. 15, 2nd ed., pp. 204 308 Silicones, year 1989.
Francis Ignatious, Linghong Sun, Chao-Pin Lee, and John Baldoni. Electrospun Nanofibers in Oral Drug Delivery—ExpertReview. Pharmaceutical Research, vol. 27, No. 4, Apr. 2010, pp. 576-588. Published online Feb. 9, 2010.
Gemz Hair Care. Perfect Pairs. Publication date unavailable. Visited Jan. 26, 2022. https://shopgemz.com/collections/perfect-pairs (Year: 0).
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hildebrand, T., et al. "Quantification of bone microarchitecture with the structure mode index", Computer Methods in Biomechanics and Biomedical Engineering, vol. 1, Jan. 14, 1997, pp. 15-23.
Hiroshi Yagi & 4 Others, Research Study of a Friction Protector for Preventing a Tow Line From Breaking,Working Papers for Fiscal 2006 | Japan | Japan Coast Guard |Dec. 2007, pp. 1-8.
How Gemz work?, Gemz Hair Care, published on Oct. 1, 2018, retrieved on Apr. 27, 2021, retrieved from the Internet URL: https://www.youtube.com/watch?v=ts1waYk43g4, 3 pgs.
Karen Duis et al, "Environmental fate and effects of water-soluble synthetic organic polymers used in cosmetic products", Environmental Sciences Europe, vol. 33, Article No. 21, Feb. 16, 2021, 78 pages.
Latorre Carmen, Nanotribological Effects of Hair Careproducts and Environment on Human Hair Using Atomic Forcemicroscopy, Journal of Vacuum Science and Technology: Part A, U.S.A, AVS/AIP, Jun. 28, 2005 , V2 3 N 4, p. 1034-1045.

Makadia, et al., "Poly Lactic-co-Glycolic Acid (PLGA) as Biodegradable ControlledDrug Delivery Carrier", Polymers, 3, pp. 1377-1397 (2011).
Ménard et al., "Gnotobiotic Mouse Immune Response Induced by *Bifidobacterium* sp. Strains Isolated from Infants", Applied and Environmental Microbiology, vol. 74, Issue 3, Feb. 1, 2008, pp. 660-666.
Michelle Villett, Why You Need a Sulfate-Free Shampoo, The Skincare Edit, updated date: Jan. 25, 2019, Original publication date: Feb. 22, 2016 (Year: 2016), 7 pages. Mar. 23, 2021.
Minifibers, Inc., accessed on line at http://www.minifibers.com/documents/Choosing-the-Proper-Short-Cut-Fiber.pdf Oct. 3, 2016.
Ni Genshan et al. "Drug Classification and Pharmacology Summary", PLA Press, published on Apr. 30, 1988, pp. 3.
Okasaka et al., "Evaluation Of Anionic Surfactants Effects On The Skin Barrier Function Based On Skin Permeability", Pharmaceutical Development and Technology, vol. 24, No. 1, Jan. 23, 2018, pp. 99-104.
Overview of pharmaceutical excipients used in tablets and capsules in Drug Topics, dated Oct. 24, 2008. Downloaded Sep. 20, 2016 from http://drugtopics.modernmedicine.com/drugtopics/news/modernmedicine/modernmedicinenews/overviewpharmaceuticalexcipientsusedtablets.
Paper Pieces Hexagons, announced 2018 [online], [site visited Oct. 14, 2021]. Available from internet, URL:https://www.amazon.com/Paper-Pieces-HEX100B-Hexagons-1200pc/dp/B07DVYV2HN/ (Year: 2018).
Product Review: Gemz Solid Shampoo, Travel As Much, published on Mar. 19, 2019, retrieved on Apr. 27, 2021, retrieved from the Internet URL: https://travelasmuch.com/gemz-solid-shampoo-review/, 14 pgs.
Raymond C Rowe et al., Polyvinyl Alcohol, Handbook of Pharmaceutical Excipients, 2009, Sixth Edition, Pharmaceutical Press, 564-565.
Rounded hexagon shape, announced 2016 [online], [site visited Oct. 20, 2021], Available from internet, URL:https://www.vexels.com/png-svg/preview/139199/rounded-hexagon-shape (Year: 2016).
Sahin et al. "A Study on Physical and Chemical Properties of Cellulose Paper Immersed in Various Solvent Mixtures" International Journal Of Molecular Sciences, Jan. 2008; 9(1): 78-88.
Smith, et al., "Nanofibrous Scaffolds and Their Biological Effects", Nantechnologiesfor the Life Sciences, vol. 9, pp. 188-215 (2006).
Vaughan, C.D. "Solubility, Effects in Product, Package, Penetration and Preservation", Cosmetics and Toiletries, vol. 103, Oct. 1988, 24 pgs.
Vesterby, A.: "Star Volume in Bone Research: A Histomorphometric Analysis Of Trabecular Bone Structure Using Vertical Sections", Anal Rec: Feb. 1993, 232(2), pp. 325-334.
W S Ratnayake and D S Jackson. Gelatinization and solubility of corn starch during heating in excess water. Facultyu Publications in Food Science and Technology, Jan. 1, 2006. Also published in Journal of Agricultural and Food Chemistry 54:1 O(2006), pp. 3712-3716.
Wang, et al., "A Novel Controlled Release Drug Delivery System for Multiple DrugsBased on Electrospun Nanofibers Containing Nanoparticles", Journal ofPharmaceutical Sciences, vol. 99, No. 12 (Dec. 2010).
Wermuth et al. Drug Discovery, "Drug Discovery Today, 2006", vol. 11 7/8, 348-354, Year 2006.
Yasuhiro Hiramatsu et al. "Bifidobacterium Components Have Immunomodulatory Characteristics Dependent on the Method of Preparation" Cytotechnology, Kluwer Academic Publishers, Do, vol. 55, Issue No. 2-3, Nov. 1, 2007, p. 79-87.
Zhang et al. "Study on Morphology of Electrospun Poly( vinyl alcohol) Mats," European Polymer Journal 41 (2005), pp. 423-432.
Pattama Taepalboon, et al., "Effect of Cross-linking on Properties and Release Characteristics of Sodium Salicylate-loaded Electrospun Poly(Vinyl Alcohol) Fibre Mats", Nanotechnology, vol. 18, No. 17, Apr. 2, 2007.
Wikipedia "Polyvinyl alcohol," URL Link—https://en.wikipedia.org/wiki/Polyvinyl_alcohol, dated May 25, 2017, 5 pgs.

\* cited by examiner

WATER-SOLUBLE FIBROUS POUCH CONTAINING PRILLS FOR HAIR CARE

FIELD OF THE INVENTION

The present invention relates to pouches, more particularly to water-soluble fibrous pouches that are made from fibrous sheets sealed around a perimeter to form an internal volume that contains a plurality of prills comprising one or more personal care actives.

BACKGROUND OF THE INVENTION

Many in market personal care and other consumer products, including shampoo and conditioners, are sold in liquid form. While widely used, liquid products often have tradeoffs in terms of packaging, storage, transportation, and convenience of use. For example, these products are generally formulated with a substantial amount of water (e.g. ~80% or more), preservatives, and stabilizers, that add significant bulk and translates to inefficient, costly shipping and storage. Also, liquid personal care products can also be difficult to use in terms of controlling dosage and the delivery of the product.

In order to overcome some of these drawbacks, it can be desirable to formulate personal care products as solid articles that can include dissolvable films, compressed powders in a solid, fibrous articles, porous foams, soluble deformable solids, powders, bars or prills. However, many of these executions are not ideal for consumers. For example, some products including many bars or prills, do not hydrate and dissolve fast enough when exposed to water to satisfy the consumer's desire to quickly apply a homogeneous liquid product to the hair, scalp, and/or body, without undue effort to dissolve the product. Furthermore, if prills are small enough to hydrate quickly, they can be inconvenient and messy to dispense and use. Other executions, including some fibrous articles containing conditioner actives, melt at temperatures greater than 45° C., which can be encountered during shipping, handling, after in-store purchase in a consumer's hot car, after online purchase or the article may sit in her mailbox or at the front door, and/or during storage in non-temperature-controlled storage areas (e.g. warehouse, consumer's garage etc.). Melted articles can resolidify, however, it has been found that the dissolution can be significantly slowed and when the article finally dissolves, it can dissolve into a grainy paste, instead of a rich, creamy personal care product.

As such, there remains a need for an easy to use, solid personal care article that has a melt point greater than 45° C. and rapidly disintegrates into a smooth, creamy, homogeneous product upon hydration.

SUMMARY OF THE INVENTION

A water-soluble pouch for hair care comprising: (a) a water-soluble pouch defining an internal volume comprising: (i) a water-soluble fibrous facing sheet comprising a perimeter, an outer surface, and an inner surface; and (ii) a water-soluble fibrous backing sheet comprising a perimeter, an outer surface, and an inner surface; wherein the facing sheet and the backing sheet comprise a thermal seal joining the facing sheet to the backing sheet along at least a portion of the perimeters; wherein the fibrous structure comprises a plurality of two or more fibrous elements that are inter-entangled or otherwise associated with one another; wherein the fibrous elements comprise a polymeric structurant that is thermally sealable without the addition of an adhesive or other composition; wherein the outer surfaces and/or the inner surfaces of the facing and backing sheets comprise a plurality of bonding points; (b) a plurality of prills within the internal volume comprising: (i) from about 1% to about 60%, by weight of the prills, of a cationic surfactant selected from the group consisting of behentrimonium methosulfate, brassicamidopropyl dimethylamine, behentrimonium chloride, stearamidopropyl dimethylamine, and/or behenamidopropyl dimethylamine; (ii) from about 10% to about 90%, by weight of the prills, of a fatty alcohol; wherein the prills comprise a melting point of greater than 45° C.

A water-soluble pouch for hair care comprising: (a) a water-soluble fibrous pouch defining an internal volume; (i) a water-soluble fibrous facing sheet comprising a perimeter, an outer surface, and an inner surface; and (ii) a water-soluble fibrous backing sheet comprising a perimeter, an outer surface, and an inner surface; wherein the facing sheet and the backing sheet are sealed along the perimeters to form a pouch defining an internal volume; wherein the fibrous structure comprises a plurality of two or more fibrous elements that are inter-entangled or otherwise associated with one another; wherein the fibrous elements comprise a polymeric structurant selected from the group consisting of starch, cellulose, hemicellulose, polyvinyl alcohol, and mixtures and derivatives thereof; wherein the facing sheet and the backing sheet comprise a seal permanently joining the facing sheet to the backing sheet along at least a portion of the perimeters; wherein the facing sheet and the backing sheet are substantially free of apertures; (b) a plurality of prills within the internal volume comprising: (i) from about 1% to about 60%, by weight of the prills, of a cationic surfactant selected from the group consisting of behentrimonium methosulfate, brassicamidopropyl dimethylamine, behentrimonium chloride, stearamidopropyl dimethylamine, and/or behenamidopropyl dimethylamine; (ii) from about 10% to about 90%, by weight of the prills, of a fatty alcohol; wherein the prills dissolve to form a gel network; wherein the pouch comprises a melting point of greater than 45° C.

A water-soluble pouch for hair care comprising: (a) a water-soluble pouch defining an internal volume comprising: (i) a water-soluble fibrous facing sheet comprising a perimeter, an outer surface, and an inner surface; and (ii) a water-soluble fibrous backing sheet comprising a perimeter, an outer surface, and an inner surface; wherein the facing sheet and the backing sheet comprise a thermal seal joining the facing sheet to the backing sheet along at least a portion of the perimeters; wherein the fibrous structure comprises a plurality of two or more fibrous elements that are inter-entangled or otherwise associated with one another; wherein the fibrous elements comprise a polymeric structurant that is thermally sealable without the addition of an adhesive or other composition; wherein the outer surfaces and/or the inner surfaces of the facing and backing sheets comprise a plurality of bonding points; (b) a plurality of prills within the internal volume comprising: (i) from about 1% to about 60%, by weight of the prills, of an anionic surfactant; (ii) optionally a zwitterionic co-surfactant selected from the group consisting of cocoamiodpropyl betaines, lauramidopropyl betaine, and combinations thereof; wherein the prills comprise a melting point of greater than 45° C.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
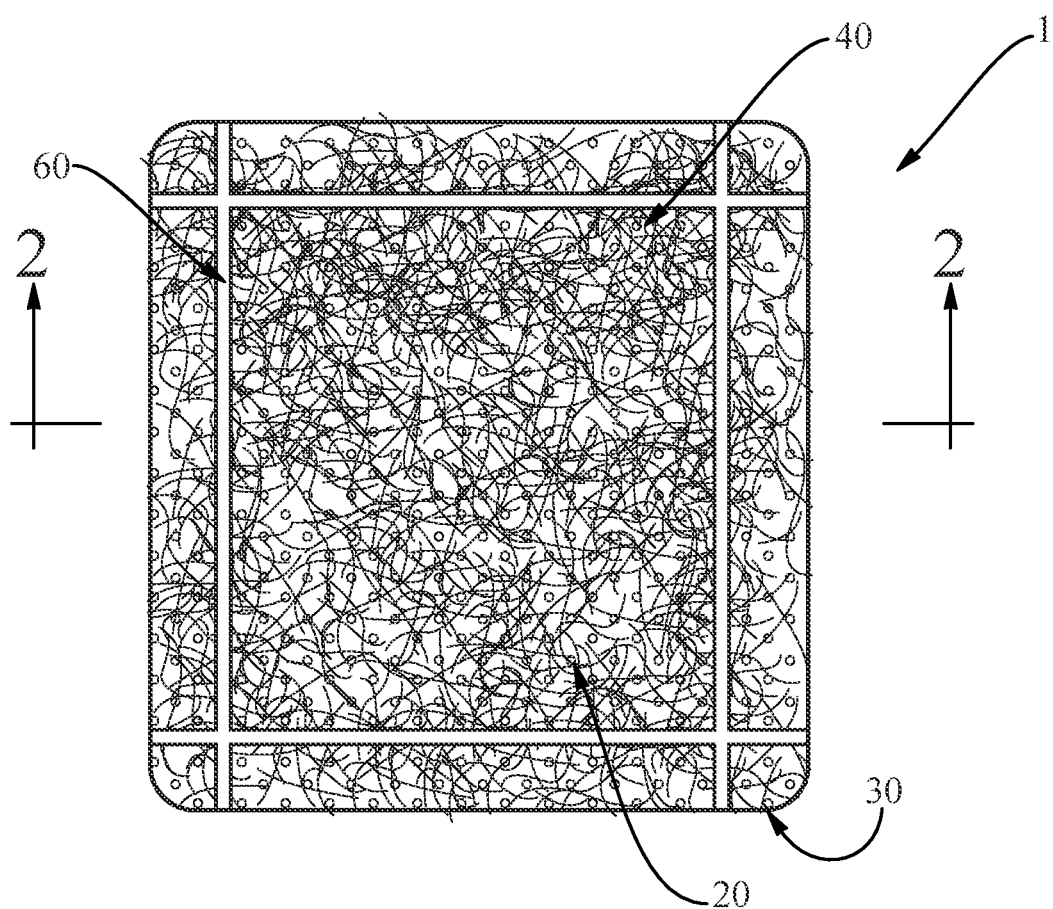
FIG. 1 is a schematic representation of a top view of a water-soluble pouch containing prills.

There are many advantages to using a solid personal care article, such as shampoo or conditioner, instead of traditional liquid compositions. For instance, solid personal care articles are less expensive to ship because solid articles can be substantially free of water, preservatives, and stabilizers. Furthermore, solid personal care articles can be easier to control the dosing and delivery of the product and in some instances, actives that are generally incompatible in a liquid composition can be stable in a solid article.

However, a drawback to solid articles is that they can take a long time to dissolve and users are impatient, especially when they are hydrating a solid article in their hands while in the shower, bath, or at a sink, where a relatively short period of time (e.g. 15-20 seconds), can feel like an eternity.

It has been found that articles made from fibrous structures, such as those described in US Pub. Nos. 2018/0333339 and 2019/0282461, incorporated by reference, can provide excellent dissolution. However, some of these articles can melt when exposed to temperatures>45° C. Articles can be exposed to these high temperatures during shipping and handling and after purchase (e.g. a consumer may leave the personal care articles in her car when she runs other errands on a hot summer day or the articles can be order through e-commerce and left outside the front door or in a hot mailbox).

For example, articles made from fibrous structures with conditioner actives can contain an acyl glucamide because it can prevent the polyvinylpyrrolidone (PVP) structurant from reacting with other conditioning actives, which can enable the structure to have consumer acceptable swelling, dissolution, and conditioning. However, the acyl glucamide lowers the melting temperature of the entire structure and the structure can melt when exposed to temperatures greater than 45° C. Furthermore, when the melted article resolidifies, it was found that the article may not hydrate and dissolve at a rate that is consumer acceptable and when it does, it can have an unpleasant grainy texture.

Frills have a large surface area to volume, which can make dissolution faster than other solid forms. However, it is still difficult to formulate and manufacture prills so they have a consumer preferred quick dissolution (e.g. less than ~5 seconds). Even if prills have a fast-enough dissolution, they can be cumbersome to use. First in order to use prills, a user may need to pour them from a larger container. This provides no benefit for dosing over a regular liquid personal care product. Also, personal care compositions, especially shampoo, conditioner, body wash, and other soaps are generally used in a humid shower or bathroom or near running water and the user would need to prevent humidity from entering the bottle and dissolving the prills. Also, in order to get fast dissolution, prills need to be relatively small and some could become airborne when poured from the container, making a mess.

In order to overcome some of the disadvantages of prills, it was found that the prills could be delivered in a pouch, such as a water-soluble pouch made from one or more fibrous sheets. When the pouch is exposed to water, the fibrous sheet(s) and water-soluble prills quickly dissolve into a homogenous, uniform, smooth, creamy, liquid personal care composition, such as a shampoo or a creamy conditioner. In some instances, the pouch seems to dissolve instantaneously. The water-soluble pouch can have a hand dissolution value of from about 1 to about 30 strokes, alternatively from about 2 to about 25 strokes, alternatively from about 3 to about 20 strokes, alternatively from about 4 to about 15 strokes, alternatively from about 5 to about 10 strokes, as measured by the Hand Dissolution Method, described hereafter. The water-soluble pouch can have a hand dissolution value of less than 25 strokes, alternatively less than 20 strokes, alternatively less than 15 strokes, alternatively less than 12 strokes, alternatively less than 10 strokes, alternatively less than 8 strokes, as measured by the Hand Dissolution Method, described hereafter.

The pouch can contain enough prills to sufficiently clean and/or condition a user's hair while providing a good user experience without rupturing the bonding points on the pouch. The weight ratio of prills to fibrous sheet(s) can be from about 1:1 to about 10:1, alternatively from about 2:1 to about 8:1, alternatively from about 3:1 to about 6:1, and alternatively from about 4:1 to about 5:1. In one example the weight ratio of prills to fibrous sheet(s) is about 4.5:1. The weight ratio of prills to fibrous sheet(s) can be less than 7:1, alternatively less than 6:1, alternatively less than 5.5:1, alternatively less than 5:1, alternatively less than 4.75:1, alternatively less than 4:1.

The pouch can fit in the palm of a user's hand. The pouch can have a length from about 0.5 in (1.27 cm) to about 6 in (15.24 cm), alternatively from about 1 in (2.54 cm) to about 4 in (10.16 cm), alternatively from about 1.5 in (3.81 cm) to about 3.5 in (8.89 cm), alternatively from about 1.75 in (4.45 cm) to about 3 in (7.62 cm), and alternatively from about 2 in (5.08 cm) to about 2.5 in (6.35 cm). The facing sheet and/or backing sheet can have a surface area from about 2 $in^2$ (12.90 $cm^2$) to about 6 $in^2$ (38.71 $cm^2$), alternatively from about 3 $in^2$ (19.35 $cm^2$) to about 5 $in^2$ (32.27 $cm^2$), alternatively from about 3.5 $in^2$ (22.58 $cm^2$) to about 4.5 $in^2$ (29.03 $cm^2$), alternatively from about 3.75 $in^2$ (24.19 $cm^2$) to about 4.25 $in^2$ (27.42 $cm^2$)

The pouch can contain about 0.5 to about 5 grams of prills, alternatively from about 1 to about 4 grams of prills, alternatively from about 1.5 to about 3 grams of prills, and alternatively about 2 grams of prills.

Figure 2:
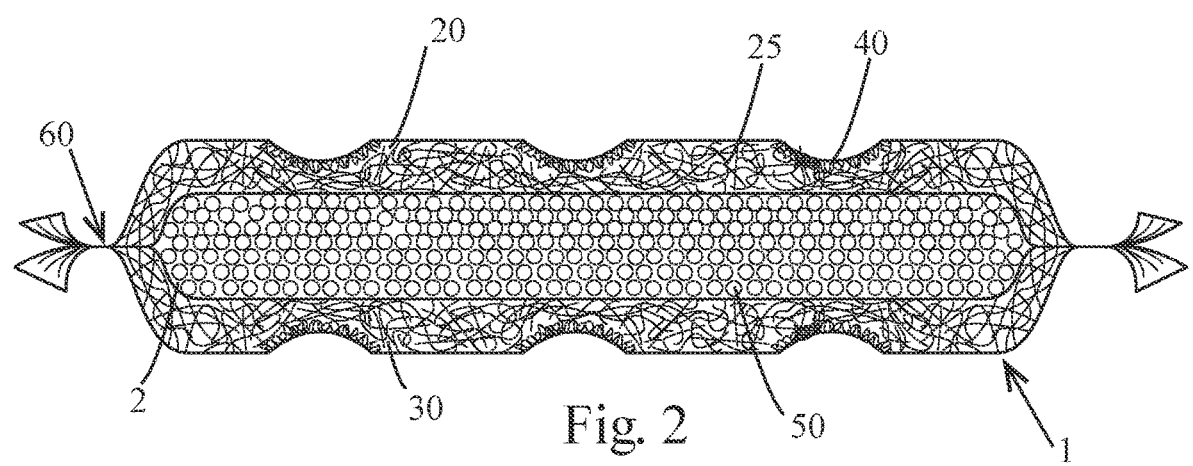
FIG. 2 is a schematic representation of an enlarged cross-sectional view of the water-soluble pouch taken along section line 2-2 in FIG. 1.

FIGS. 1 and 2 shows a water-soluble pouch 1 enclosing an internal volume 2 that can contain prills 50. Pouch 1 is made from water-soluble fibrous facing sheet 20 with a perimeter and water-soluble fibrous backing sheet 30 with a perimeter. Facing sheet and backing sheet 30 can be two separate water-soluble fibrous sheets or the same piece of water-soluble fibrous sheet with a perimeter can be folded to form facing sheet and backing sheet. The facing sheet and backing sheet can have the same composition or different compositions.

Facing sheet 20 and backing sheet 30 can be joined (e.g. permanently joined) along at least a portion of their perimeters by seal 60 to form a pouch. The front and back facing sheets can be sealed by any sealing means. For example, by thermal sealing, wet sealing or by pressure sealing. In some examples, seal 60 is a thermal seal. The seal can be dissolvable. The pouch can be formed without the use of adhesives or sewing. The water-soluble fibrous facing and backing sheets can be sealed together in such a manner as to at least partially enclose and/or completely enclose its internal volume and the prills containing active agents within its internal volume.

In another example, the pouch making process may be used to prepare pouches which have an internal volume that is divided into more than one compartment, typically known as a multi-compartment pouch.

The water-soluble facing and backing sheet can be the same material and structure and/or they can be different materials or structures. The outer surface and/or the inner surface of the facing sheet and the backing sheet can each have a plurality of bonding points 40. Bonding the facing sheet and the backing sheet can help improve performance of the article by strengthening the pouch by melting the fibrous elements together and preventing the prills from leaking out of the pouch between the fibrous elements. The bonding points can extend completely or partially through the facing sheet and/or the backing sheet. The facing sheet and/or the backing sheet can have 5-25 10-20 bonding points per $cm^2$, alternatively 10-20 bonding points per $cm^2$, and alternatively 10-15 bonding points per $cm^2$. In some examples, the facing sheet and/or the backing sheet may be substantially free of apertures.

The water-soluble facing and/or backing sheets can include a dissolvable fibrous structure to form water-soluble fibrous sheet(s). The fibrous structure can be non-continuous, unlike a film that can be a continuous sheet. The fibrous structure may neither a film nor a foam, such as an open-cell foam or a closed-cell foam. The fibrous structure can include a plurality of two or more fibrous elements that are interentangled or otherwise associated with one another to form a fibrous structure. The fibrous elements can be made from a fibrous element forming composition that contains one or more filament-forming materials, which can be a polymeric structurant that can be spun into filaments and can dissolve smoothly and quickly. The polymeric structurant can form a seal (e.g. thermal seal) without adding adhesive or other components. The polymeric structurant can include natural polymers, such as starch, starch derivatives, cellulose, such as rayon and/or lyocell, and cellulose derivatives, hemicellulose, and hemicellulose derivatives. Typical sources for starch can include cereals, tubers, roots, legumes and fruits. The starch source can be a native source including corn, pea, potato, banana, barley, wheat, rice, sago, amaranth, tapioca, arrowroot, canna, sorghum, and waxy or high amylase varieties thereof. The polymeric structurant can also contain polyvinyl alcohol.

Prills 50 can be disposed between facing sheet 20 and backing sheet 30. The prills and/or the pouch may not melt if they resolidified after melting at a high temperature during shipping, handling, transport, and/or storage. The prills and/or pouch can have a melting point of greater than 40° C., alternatively greater than 45° C., alternatively greater than 48° C., alternatively greater than 50° C., alternatively greater than 55° C., alternatively greater than 60° C. The melting point can be determined according to the Melting Point Test Method, described hereafter.

The prills can be formulated so they are water-soluble, have a relatively high melting point, relatively fast dissolution rate, and dissolve to form a creamy and/or homogeneous composition. The prills can all have substantially the same composition or the prills can have different compositions. For example, the prills disposed in a pouch can have different actives. The prills can contain actives, such as shampoo and conditioning actives, that can be used to clean, condition, and/or otherwise nourish a person's hair.

A surfactant can be an active. For instance, if the pouch is intended to be used as a shampoo, the active may include one or more anionic surfactants and optionally a cosurfactant, such as a zwitterionic cosurfactant. The pouch, including the prills and/or fibrous sheets, can be substantially free of surfactants with chain lengths less than or equal to 14 including, but not limited to, sodium laureth sulfate (e.g. SLES and SLE1S), sodium lauryl sulfate (SLS), cocoamidopropyl betaines (CAPB), lauramidopropyl betaine.

If the pouch is intended to be used as a conditioner, the active may include one or more cationic surfactants and/or one or more fatty alcohols. The prill can contain the cationic surfactant and fatty alcohol and the fibrous sheets can be substantially free of cationic surfactant and/or fatty alcohol. The cationic surfactant can be a C16-C18 cationic surfactant, for example behentrimonium methosulfate, brassicamidopropyl dimethylamine, behentrimonium chloride, stearamidopropyl dimethylamine, and/or behenamidopropyl dimethylamine (BAPDMA). The pouch, including the fibrous sheet(s) and the prills, can be substantially free of cationic surfactants with a C12-C14 chain length. The fatty alcohol can include cetyl and/or stearyl alcohol. The pouch, including the fibrous sheet(s) and/or the prills, can be substantially free of glucamides, in particular alkyl glucamides. Acyl glucamide may be selected from the group consisting of lauroyl/myristoyl methyl glucamide, capryloyl/capryloyl methyl glucamide, cocoyl methyl glucamide and mixtures thereof.

The pouch and/or prills can have a molar ratio of cationic surfactant to fatty alcohol that can provide a nice creamy product that has a viscosity that is no too thick, so the product is tough to spread and not too thin, so the product is difficult to hold in a user's hand. The molar ratio of cationic surfactant to fatty alcohol can be from about 1:20 to about 1:1, alternatively from about 1:8 to about 4:5, alternatively from about 1:7 to about 2:3, alternatively from about 1:6 to about 3:5, and alternatively from about 1:5 to about 1:3.

The prills can be small enough that a plurality of prills can be free flowing, but not so small that the particles stick together. Flow aides can be included at low levels on the surface of the prill to help prills flow better, non-limiting examples include Zeolite A, precipitated silica, precipitated silicates, fly ash, talc, starch, clays, metallic stearates, phosphates, amides, polysaccharides, sugars, and combinations thereof. Particularly suitable materials include Zeolite A, silica, sugars and mixtures thereof. The flowability of the prills can be determined at 96 hours to determine if the prills are free flowing or consolidated.

The prills can have an average length of less than 1 mm, alternatively less than 750 μm, alternatively less than 600 μm, alternatively less than 500 μm, alternatively less than 400 μm, alternatively less than 300 μm, and alternatively less than 250 μm. The prills can have an average length from about 50 μm to about 1000 μm, alternatively from about 100 μm to about 800 μm, alternatively from about 150 μm to about 700 μm, alternatively from about 200 μm to about 600 μm, and alternatively from about 250 μm to about 500 μm. The average length of the prill can be determined by the Median Particle Size Test Method, described hereafter. In some examples, the prills can be spherical and the length can be a diameter. In some examples, the prills are not agglomerated.

The pouch can have a basis weight of less than 250 grams/m², alternatively less than 200 grams/m², alternatively less than 150 grams/m², alternatively less than 125 grams/m², less than 100 grams/m², and alternatively less than 80 grams/m². The pouch can have a basis weight of from about 20 to about 250 grams/m², alternatively from about 30 to about 200 grams/m², alternatively from about 30 to about 150 grams/m², alternatively from about 40 to about 120 grams/m², alternatively from about 50 to about 100 grams/m². The basis weight is determined by the Basis Weight Test Method, described hereafter.

Definitions

"Dissolvable" means that the pouch, prills, and/or fibrous sheet(s) are completely soluble in water or it provides a uniform dispersion upon mixing in water according to the Hand Dissolution Test, described hereafter.

"Fibrous structure" as used herein means a structure that comprises one or more fibrous elements. In one example, a fibrous structure according to the present invention means an association of fibrous elements together form a structure, such as a unitary structure or sheet. In some examples, the fibrous structure can further comprise particles. The fibrous structures of the present invention may be homogeneous or may be layered. If layered, the fibrous structures may comprise at least two and/or at least three and/or at least four and/or at least five layers, for example one or more fibrous element layers, one or more particle layers and/or one or more fibrous element/particle mixture layer.

In one example, the fibrous structure of the present invention can be a "unitary fibrous structure" and/or the facing sheet and/or the backing sheet can be a "unitary fibrous structure."

"Unitary fibrous structure" as used herein is an arrangement comprising a plurality of two or more and/or three or more fibrous elements that are inter-entangled or otherwise associated with one another to form a fibrous structure. A unitary fibrous structure of the present invention may be one or more plies within a multi-ply fibrous structure. In one example, a unitary fibrous structure of the present invention may comprise three or more different fibrous elements. In another example, a unitary fibrous structure of the present invention may comprise two different fibrous elements, for example a co-formed fibrous structure, upon which a different fibrous element is deposited to form a fibrous structure comprising three or more different fibrous elements.

"Fibrous element" as used herein means an elongate particulate having a length greatly exceeding its average diameter, i.e. a length to average diameter ratio of at least about 10. A fibrous element may be a filament or a fiber. In one example, the fibrous element can be a single fibrous element rather than a yarn comprising a plurality of fibrous elements.

The fibrous elements of the present invention may be spun from a filament-forming composition also referred to as fibrous element-forming compositions via suitable spinning process operations, such as meltblowing, spunbonding, electro-spinning, and/or rotary spinning.

The fibrous elements of the present invention may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present invention and then cutting the filament or filament tow into segments of less than 5.08 cm (2 in.) thus producing fibers.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more polymeric structurants and one or more other ingredients, including but not limited to a plasticizer and/or a water-soluble active ingredient such as histidine. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" and/or "fibrous element-forming composition" as used herein means a composition that can be suitable for making a fibrous element of the present invention such as by meltblowing and/or spunbonding. The filament-forming composition comprises one or more polymeric structurants that exhibit properties that make them suitable for spinning into a fibrous element. In addition, the filament-forming composition may comprise one or more polar solvents, such as water, into which one or more, for example all, of the polymeric structurant and/or one or more, for example all, of surfactants are dissolved and/or dispersed prior to spinning a fibrous element, such as a filament from the filament-forming composition.

In one example, one or more additives, such as active agents, may be present in the fibrous element and/or the prills and/or particles one or more additional additives, such as active agents, may be present on a surface of the fibrous element and/or prills and/or particles. In another example, a fibrous element of the present invention may comprise one or more additives, such as active agents, that are present in the fibrous element when originally made, but then bloom to a surface of the fibrous element prior to and/or when exposed to conditions of intended use of the fibrous element.

As used herein, "vinyl pyrrolidone copolymer" (and "copolymer" when used in reference thereto) refers to a polymer of the following structure (I):

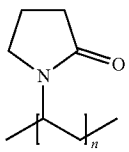 (I)

In structure (I), n is an integer such that the polymeric structurant has the degree of polymerization such that it possesses characteristics described herein. For purposes of clarity, the use of the term "copolymer" is intended to convey that the vinyl pyrrolidone monomer can be copolymerized with other non-limiting monomers such as vinyl acetate, alkylated vinyl pyrrolidone, vinyl caprolactam, vinyl valerolactam, vinyl imidazole, acrylic acid, methacrylate, acrylamide, methacrylamide, dimethacrylamide, alkylaminomethacrylate, and alkylaminomethacrylamide monomers.

As used herein, "vinyl acetate-vinyl alcohol copolymer" (and "copolymer" when used in reference thereto) refers to a polymer of the following structure (I):

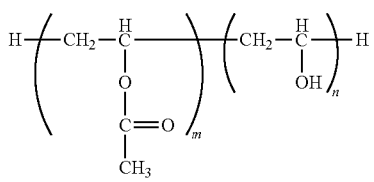 (I)

In structure (I), m and n are integers such that the polymeric structurant has the degree of polymerization and percent alcohol characteristics described herein. For purposes of clarity, this use of the term "copolymer" is intended to convey that the partially hydrolyzed polyvinyl acetate of the present invention comprises vinyl alcohol and vinyl acetate units. As discussed below, the polymeric structurant is routinely prepared by polymerizing vinyl acetate monomer followed by hydrolysis of some of the acetate groups to alcohol groups, as opposed to polymerization of vinyl acetate and vinyl alcohol monomer units (due in-part to the instability of vinyl alcohol).

"Particle" as used herein means a solid additive, in addition to the prills that contain surfactant, and includes powder, granule, encapsulate, additional prills and/or microcapsule. The pouch can contain particles in the internal volume and/or they can be within or on the surface of the facing sheet and/or backing sheet. In one example, the particle exhibits a median particle size of 1000 µm or less as measured according to the Median Particle Size Test Method described herein. In another example, the particle exhibits a median particle size of from about 1 µm to about 1000 µm and/or from about 1 µm to about 800 µm and/or from about 5 µm to about 500 µm and/or from about 10 µm to about 400 µm and/or from about 10 µm to about 300 µm and/or from about 10 µm to about 250 µm as measured according to the Median Particle Size Test Method described herein. The shape of the particle can be in the form of spheres, rods, plates, tubes, squares, rectangles, discs, stars, fibers or have regular or irregular random forms.

"Active agent-containing particle" as used herein means a solid additive comprising one or more active agents. In one example, the active agent-containing particle can be an active agent in the form of a particle (in other words, the particle comprises 100% active agent(s)). In one example, the active agent-containing particle can contain perfume and/or silicone. The active agent-containing particle may exhibit a median particle size of 1600 µm or less as measured according to the Median Particle Size Test Method, described herein. In another example, the active agent-containing particle exhibits a median particle size of from about 1 µm to about 1600 µm and/or from about 1 µm to about 800 µm and/or from about 5 µm to about 500 µm and/or from about 10 µm to about 300 µm and/or from about 10 µm to about 100 µm and/or from about 10 µm to about 50 µm and/or from about 10 µm to about 30 µm as measured according to the Median Particle Size Test Method described herein. In one example, one or more of the active agents can be in the form of a particle that exhibits a median particle size of 20 µm or less as measured according to the Median Particle Size Test Method described herein.

"Conditions of intended use" as used herein means the temperature, physical, chemical, and/or mechanical conditions that a fibrous element and/or particle and/or fibrous structure of the present invention is exposed to when the fibrous element and/or particle and/or fibrous structure is used for one or more of its designed purposes. For instance, if a fibrous element and/or a particle and/or a fibrous structure comprising a fibrous element is designed to be used by a human as a shampoo for hair care purposes, the conditions of intended use will include those temperature, chemical, physical and/or mechanical conditions present during the shampooing of the human's hair. Likewise, if a fibrous element and/or a particle and/or a fibrous structure comprising a fibrous element is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active" or "active agent" as used herein means an additive that produces an intended effect in an environment external to a fibrous element and/or a prill and/or a fibrous structure and/or pouch and/or fibrous sheet(s) when exposed to conditions of intended use. In one example, an active agent comprises an additive that treats a surface, including a soft surface (i.e., hair, skin). In another example, an active agent comprises an additive that creates a chemical reaction (i.e., foaming, fizzing, coloring, warming, cooling, lathering, disinfecting and/or clarifying). In yet another example, an active agent comprises an additive that treats an environment (i.e., deodorizes, purifies, perfumes). In one example, the active agent is formed in situ, such as during the formation of the fibrous element and/or prill containing the active agent, for example the fibrous element and/or particle may comprise a water-soluble polymer (e.g., starch) and/or a surfactant (e.g., anionic surfactant), which may create a polymer complex or coacervate that functions as the active agent used to treat the hair and/or scalp.

"Treats" as used herein with respect to treating a surface means that the active agent provides a benefit to a surface or environment. Treats includes regulating and/or immediately improving a surface's, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

"Weight ratio" as used herein means the ratio between two materials on their dry basis.

"Water-soluble material" as used herein means a material that is miscible in water. In other words, a material that is capable of forming a stable (does not separate for greater than 5 minutes after forming the homogeneous solution) homogeneous solution with water at ambient conditions.

"Water-insoluble" as used herein is meant that the material, particle/prill, and/or pouch does not dissolve in or readily break apart upon immersion in water. In some instances, water-insoluble materials swell when exposed to water.

"Ambient conditions" as used herein means 23° C.±1.0° C. and a relative humidity of 50% ±2%.

As used herein, "molecular weight" or "M.Wt." refers to the weight average molecular weight unless otherwise stated. Molecular weight is measured using industry standard method, gel permeation chromatography ("GPC").

"Length" as used herein, with respect to a fibrous element, means the length along the longest axis of the fibrous element from one terminus to the other terminus. If a fibrous element has a kink, curl or curves in it, then the length is the length along the entire path of the fibrous element from one terminus to the other terminus.

"Diameter" as used herein, with respect to a fibrous element, is measured according to the Diameter Test Method described herein. In one example, a fibrous element of the present invention exhibits a diameter of less than 100 µm and/or less than 75 µm and/or less than 50 µm and/or less than 25 µm and/or less than 20 µm and/or less than 15 µm and/or less than 10 µm and/or less than 6 µm and/or greater than 1 µm and/or greater than 3 µm.

"Triggering condition" as used herein in one example means anything, as an act or event, that serves as a stimulus and initiates or precipitates a change in the fibrous element and/or prill(s) and/or pouch, such as a loss or altering of the fibrous element's and/or prill(s)'s and/or pouch's physical structure and/or a release of an additive, such as an active agent therefrom. In another example, the triggering condition may be present in an environment, such as water, when a fibrous element and/or prill(s) and/or pouch of the present invention is added to the water. In other words, nothing changes in the water except for the fact that fibrous element and/or prill(s) and/or pouch of the present invention is added to the water.

"Morphology changes" as used herein with respect to a fibrous element's and/or prill(s)'s and/or pouch's morphology changing means that the fibrous element and/or particle/prill(s) experiences a change in its physical structure. Non-limiting examples of morphology changes for a fibrous element and/or particle/prill of the present invention include dissolution, melting, swelling, shrinking, breaking into pieces, exploding, lengthening, shortening, and combinations thereof. The fibrous elements and/or particles of the present invention may completely or substantially lose their fibrous element or particle/prill physical structure or they may have their morphology changed or they may retain or substantially retain their fibrous element or particle physical structure as they are exposed to conditions of intended use.

"By weight on a dry fibrous element basis" and/or "by weight on a dry particle basis" and/or "by weight on a dry fibrous structure basis" means the weight of the fibrous element and/or particle and/or fibrous structure, respectively, measured immediately after the fibrous element and/or particle and/or fibrous structure, respectively, has been conditioned in a conditioned room at a temperature of 23° C.±1.0° C. and a relative humidity of 50%±10% for 2 hours. In one example, by weight on a dry fibrous element basis and/or dry particle basis and/or dry fibrous structure basis means that the fibrous element and/or particle and/or fibrous structure comprises less than 20% and/or less than 15% and/or less than 10% and/or less than 7% and/or less than 5% and/or less than 3% and/or to 0% and/or to greater than 0% based on the dry weight of the fibrous element and/or particle and/or fibrous structure of moisture, such as water, for example free water, as measured according to the Water Content Test Method described herein.

"Substantially free" as used herein, means that the fibrous element(s) and/or sheets, and/or prills, and/or particles, and/or pouch comprises less than 2%, alternatively less than 1.5%, alternatively less than 1%, alternatively less than 0.5%, alternatively less than 0.3%, alternatively less than 0.2%, alternatively less than 0.1%, alternatively less than about 0.05%, alternatively less than about 0.01%, alternatively free of. Alternatively, "substantially free" means that the fibrous elements, and/or sheets, and/or prills, and/or particles do not contain enough of a particular composition or compositions to increase the melting point to below 45° C., alternatively to below 50° C.

"Total level" as used herein, for example with respect to the total level of one or more active agents present in the fibrous element and/or sheet(s) and/or prills and/or pouch, means the sum of the weights or weight percent of all of the subject materials, for example active agents. In other words, a fibrous element and/or sheet(s) and/or prills and/or pouch structure may comprise 25% by weight on a dry fibrous element basis and/or dry particle basis and/or dry fibrous structure basis of a surfactant, 15% by weight on a dry fibrous element basis and/or dry particle basis and/or dry fibrous structure basis of a nonionic surfactant, 10% by weight of a chelant on a dry fibrous element basis and/or dry particle basis and/or dry fibrous structure basis, and 5% by weight of a perfume a dry fibrous element basis and/or dry particle basis and/or dry fibrous structure basis so that the total level of active agents present in the fibrous element and/or particle and/or fibrous structure is greater than 50%; namely 55% by weight on a dry fibrous element basis and/or dry particle basis and/or dry fibrous structure basis.

"Associate," "Associated," "Association," and/or "Associating" as used herein with respect to fibrous elements and/or particle means combining, either in direct contact or in indirect contact, fibrous elements and/or particles such that a fibrous structure is formed. In one example, the associated fibrous elements and/or particles may be bonded together for example by adhesives and/or thermal bonds. In another example, the fibrous elements and/or particles may be associated with one another by being deposited onto the same fibrous structure making belt and/or patterned belt.

"Ply" or "Plies" as used herein means an individual fibrous structure optionally to be disposed in a substantially contiguous, face-to-face relationship with other plies, forming a multiple ply fibrous structure. It is also contemplated that a single fibrous structure can effectively form two "plies" or multiple "plies", for example, by being folded on itself.

As used herein the term "permanently joined" refers to a connection that cannot be unattached without at least partially destroying one of the attached components.

As used herein, the articles "a" and "an" when used herein, for example, "an anionic surfactant" or "a fiber" is understood to mean one or more of the materials that is claimed or described.

As used herein, the terms "include," "includes," and "including," are meant to be non-limiting.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise noted, all component or composition levels are in reference to the active level of that component or composition, and are exclusive of impurities, for example, residual solvents or by-products, which may be present in commercially available sources.

Water-Soluble Fibrous Pouches

The water-soluble fibrous pouches can be made from one or more fibrous sheets where the fibrous elements can contain a polymeric structurant. A polymeric ingredient called a structurant increases the shear and extensional viscosity of a fluid to enable fiber formation. The structurant can be included at a level of from about 1% to about 100%, by weight of the fibrous sheet(s), alternatively from about 1% to about 98% alternatively from about 1% to about 95%, alternatively from about 2% to about 90%, alternatively from about 3% to about 88%. The structurant can be included at a level of from about 70% to about 100%, by weight of the fibrous sheet(s), alternatively from about 85% to about 97%, alternatively from about 90% to about 95%. The structurant can be included at a level of from about 60% to about 95%, by weight of the fibrous sheet(s), alternatively from about 70% to about 92%, alternatively from about 80% to about 90%.

The polymeric structurant can have a weight average molecular weight of from about 10,000 to about 6,000,000 g/mol. The weight average molecular weight is computed by summing the average molecular weights of each polymer raw material multiplied by their respective relative weight percentages by weight of the total weight of polymers present within the fibrous sheet(s). However, a balance is often struck between concentration and molecular weight, such that when a lower molecular weight species is used, it requires a higher level to result in optimal fiber spinning Likewise, when a higher molecular species is used, lower levels can be used to achieve optimal fiber spinning. The structurant having a weight average molecular weight of from about 3,000,000 g/mol to about 5,000,000 g/mol can be included at a level of from about 3% to about 6%, by weight of the fibrous sheet(s). Alternatively, a structurant having a weight average molecular weight of from about 50,000 g/mol to about 100,000 g/mol can be included at a level of from about 30% to about 50%, by weight of the fibrous sheet(s). The structurant is soluble in an oily mixture to enable viscosity build for fiber spinning. In addition, the structurant can also be soluble in water to promote removal and to prevent buildup.

The polymeric structurant can have the ability to thermally seal the edges of the pouch without the addition of an adhesive or other composition. Suitable structurants include, but are not limited to, natural polymers, such as starch, starch derivatives, cellulose, such as rayon and/or lyocell, and cellulose derivatives, hemicellulose, and hemicellulose derivatives.

The polymeric structurant can be oil soluble (fatty alcohol, fatty acid, fatty quaternary ammonium compounds) and/or water soluble. In some examples, the polymeric structurant can be water soluble with a hand dissolution score of less than 15, alternatively less than 12, alternatively less than 10, alternatively less than 8, and alternatively less than 5.

The water-soluble polymer(s) can include, but are not limited to, synthetic polymers as described in U.S. Ser. No. 61/120,786 including polymers derived from acrylic monomers such as the ethylenically unsaturated carboxylic monomers and ethylenically unsaturated monomers as described in U.S. Pat. No. 5,582,786 and EP-A-397410. In one embodiment, water-soluble polymers include polyvinyl alcohols, polyacrylates, polymethacrylates, copolymers of acrylic acid and methyl acrylate, polyvinylpyrrolidones, polyvinylmethylether, polyvinylformamide, polyacrylamide, polyalkylene oxides, starch and starch derivatives, pullulan, gelatin, hydroxypropylmethylcelluloses, methycelluloses, and carboxymethylcelluloses, salts and combinations thereof. In another embodiment, water-soluble polymers include polyvinyl alcohols, and hydroxypropylmethylcelluloses. Suitable polyvinyl alcohols include those available from Celanese Corporation (Dallas, TX) under the CELVOL® trade name. Suitable hydroxypropylmethylcelluloses include those available from the Dow Chemical Company (Midland, MI) under the METHOCEL® trade name.

Suitable structurants can also include polyvinylpyrrolidone, polydimethylacrylamides, and combinations thereof. In some examples, the polymeric structurant can be substantially free of polyvinylpyrrolidone, and/or polydimethylacrylamides.

In other examples, the polymeric structure can be capable of being produced at high weight average molecular weights. For example, suitable polymers for use are PVP K120 from Ashland Inc., having a weight average molecular weight of about 3,500,000 g/mol is soluble in the oil and water and enables fibers to be formed and collected onto a belt. Additional suitable polymers include copolymers of polyvinylpyrrolidone, such as Ganex® or PVP/VA (weight average molecular weight of about 50,000 g/mol) copolymers from Ashland Inc., also performed as suitable structurants but a higher level was utilized to be effective due to their lower weight average molecular weight. In addition, copolymers of polydimethylacrylamide also function as a suitable structurant. Hydroxyl propyl cellulose can also function as a suitable structurant.

The water-soluble fibrous pouches can be made from one or more fibrous sheets where the fibrous elements can contain a dispersing agent. The addition of a dispersing agent can greatly increase the wetting, hydration, and dispersion of the fibrous sheet(s) and/or the pouch. The dispersing agent can be included at a level of from about 1% to about 30%, by weight of the fibrous sheet(s), alternatively from about 5% to about 15%, and alternatively from about 5% to about 10%. Dispersing agents can include, but are not limited to cocoamiodpropyl betaines, alkyl glucoside, triethanol amine, cocamide monoethanolamines (MEAs) and mixtures thereof.

Plasticizer

The fibrous sheet(s) can optionally contain from about 1% to about 25% plasticizer, alternatively from about 3% to about 20% plasticizer, alternatively from about 5% to about 15% plasticizer, alternatively from about 7% to about 12%, by weight of the sheet(s). When present in the Structures, non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol, isosorbide, glucamine, N-methylglucamine and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

EP 0283165 B1 discloses suitable plasticizers, including glycerol derivatives such as propoxylated glycerol.

Prills

The prills can contain a cationic surfactant. The cationic surfactant can be included at a level from about 1% to about 60%, alternatively from about 3% to about 55%, alternatively from about 5% to about 50%, alternatively from about 7% to about 45%, alternatively from about 10% to about 40%, alternatively from about 12% to about 38%, alternatively from about 13% to about 35%, and alternatively from about 15% to about 33%, by weight of the prills.

Cationic surfactant useful herein can be one cationic surfactant or a mixture of two or more cationic surfactants. The cationic surfactant can be a cationic surfactant having one long alkyl chain of at least 16 carbon atoms, alternatively 16 to 24 carbon atoms, alternatively 16 to 22 carbon atoms, alternatively 16 to 18 carbon atoms. The cationic surfactant can be selected from the group consisting of, behentrimonium methosulfate, brassicamidopropyl dimethylamine, behentrimonium chloride, stearamidopropyl dimethylamine, and/or BAPDMA.

Mono-Long Alkyl Amine

Mono-long alkyl amine useful herein are those having one long alkyl chain of from 12 to 30 carbon atoms, alternatively from 16 to 24 carbon atoms, alternatively from 18 to 22 alkyl group. Mono-long alkyl amines useful herein also include mono-long alkyl amidoamines Primary, secondary, and tertiary fatty amines are useful.

Suitable for use in the prills are tertiary amido amines having an alkyl group of from about to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethyl amine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines can be used in combination with acids such as $\ell$-glutamic acid, lactic acid, hydrochloric acid, malic acid, succinic acid, acetic acid, fumaric acid, tartaric acid, citric acid, $\ell$-glutamic hydrochloride, maleic acid, and mixtures thereof; alternatively $\ell$-glutamic acid, lactic acid, citric acid, at a molar ratio of the amine to the acid of from about 1:0.3 to about 1:2, alternatively from about 1:0.4 to about 1:1.

Mono-Long Alkyl Quaternized Ammonium Salt

The mono-long alkyl quaternized ammonium salts useful herein are those having one long alkyl chain which has from 12 to 30 carbon atoms, alternatively from 16 to 24 carbon atoms, alternatively a C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X⁻ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, alternatively from 16 to 24 carbon atoms, alternatively from 18 to 22 carbon atoms, alternatively 22 carbon atoms; the remainder of $R^{75}$, $R^{76}$, $R^{77}$ and $R^{78}$ can be independently selected from $CH_3$, $C_2H_5$, $C_2H_4OH$, and mixtures thereof; and X can be selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts can be combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts useful herein are those having two long alkyl chains of from 12 to 30 carbon atoms, alternatively from 16 to 24 carbon atoms, alternatively from 18 to 22 carbon atoms. Such di-long alkyl quaternized ammonium salts useful herein are those having the formula (I):

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Two of $R^{71}$, $R^{72}$, $R^{73}$ and $R^{74}$ can be selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Suitable di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The prills can contain a high melting point fatty compound. The high melting point fatty compound can be included at a level of from about 5% to about 99%, alternatively from about 10% to about 97%, alternatively from about 20% to about 95%, alternatively from about 25% to about 93%, alternatively from about 28% to about 90%, alternatively from about 30% to about 88%, alternatively from about 35% to about 87%, and alternatively from about 38% to about 85%, by weight of the prills. The fatty compound can be selected from the group consisting of, but not limited to, fatty amphiphiles, fatty alcohol, fatty acid, fatty amide, fatty ester and combinations thereof.

The high melting point fatty compound useful herein have a melting point of 25° C. or higher, alternatively 40° C. or higher, alternatively 45° C. or higher, alternatively 50° C. or higher, in view of stability of the emulsion especially the gel matrix. Such melting point is up to about 90° C., alternatively up to about 80° C., alternatively up to about 70° C., alternatively up to about 65° C., in view of easier manufacturing and easier emulsification. The high melting point fatty compound can be used as a single compound or as a blend or mixture of at least two high melting point fatty compounds. When used as such blend or mixture, the above melting point means the melting point of the blend or mixture.

It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound but is done so for convenience of classification and nomenclature. Further, it is understood by the artisan that, depending on the number and position of double bonds, and length and position of the branches, certain compounds having certain required carbon atoms may have a melting point of less than the above. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols can be used in the composition described herein. The fatty alcohols useful herein are those having from about 14 to about 30 carbon atoms, alternatively from about 16 to about 22 carbon atoms. These fatty alcohols are saturated and can be straight or branched chain alcohols.

Suitable fatty alcohols include, but are not limited to, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

Generally, in the mixture, the weight ratio of cetyl alcohol to stearyl alcohol is from about 1:9 to 9:1, alternatively from about 1:4 to about 4:1, alternatively from about 1:2.3 to about 1.5:1.

When using higher level of total cationic surfactant and high melting point fatty compounds, the mixture has the weight ratio of cetyl alcohol to stearyl alcohol of from about 1:1 to about 4:1, alternatively from about 1:1 to about 2:1, alternatively from about 1.2:1 to about 2:1, in view of maintaining acceptable consumer usage. It may also provide more conditioning on damaged part of the hair.

Anionic, Non-Ionic, and Zwitterionic Surfactants The pouch and/or prills and/or particles and/or fibrous sheet(s) can contain one or more anionic, non-ionic, and/or zwitterionic surfactants suitable for application to the hair or skin. Although representative surfactants are described herein, the skilled artisan will recognize that other surfactants can be readily substituted, and similar benefits can be derived from use of the vinyl acetate-vinyl alcohol copolymers described herein. Each patent described throughout this application is incorporated herein by reference to the extent each provides guidance regarding surfactants suitable for inclusion in the Structure.

In one embodiment, the pouch is a lathering personal care product, such as a shampoo, body wash, or 2-in-1 shampoo and conditioner, can contain from about 10% to about 75% surfactant, in one embodiment from about 25% to about 70% surfactant, in another embodiment from about 40% to about 65% surfactant, by weight of the prills and/or particles and/or fibrous sheet(s) and/or pouch.

Suitable anionic surfactants include alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one embodiment, the anionic surfactant is sodium lauryl sulfate or sodium laureth sulfate.

In one embodiment, the anionic surfactant is at least one branched sulfate having the formula $CH_3$—$(CH_2)_z$—$CH(R^1)$—$CH_2$—$O$—$(CH_2CH(R^2)O)_y$—$SO_3M$; where z is from about 3 to about 14; $R^1$ represents H or a hydrocarbon radical comprising 1 to 4 carbon atoms, $R^2$ is H or $CH_3$; $R^1$ and $R^2$ are not both H; y is 0 to about 7; the average value of y is about 1 when y is not=0; and M is a mono-valent or di-valent, positively-charged cation. Examples of mono-valent positively charged cations include ammonium, sodium, potassium, triethanolamine cation, and examples of di-valent positively charged cations include magnesium. For the foregoing branched sulfates, "average value" means that whereas the composition may comprise molecules having a value of y of other than 1, the average value of y all molecules in the composition is about 1.

Suitable amphoteric or zwitterionic surfactants include those which are known for use in shampoo or other cleansing products. Non limiting examples of suitable zwitterionic or amphoteric surfactants are described in U.S. Pat. Nos. 5,104,646 and 5,106,609, which are incorporated herein by reference in their entirety.

Suitable amphoteric surfactants include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants include cocoamphoacetate, cocoamphodiacetate, lauroamphoacetate, lauroamphodiacetate, and mixtures thereof.

Suitable zwitterionic surfactants include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Suitable nonionic surfactants for use in the present invention include those described in McCutcheon's Detergents and Emulsifiers, North American edition (2010), Allured Publishing Corp., and McCutcheon's Functional Materials, North American edition (2010). Suitable nonionic surfactants for use in the Structure of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

In another embodiment, the nonionic surfactant is selected from sorbitan esters and alkoxylated derivatives of sorbitan esters including sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), sorbitan isostearate, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), all available from Uniqema, and combinations thereof.

Suitable copolymer surfactants include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

The surfactant can be a combination of surfactants wherein one or more surfactants from Group I, wherein Group I comprises anionic surfactants, and one or more surfactants from Group II, wherein Group II comprises a surfactant selected from the group consisting of amphoteric, zwitterionic and combinations thereof; wherein the ratio of Group I to Group II surfactants is from about 90:10 to about 30:70.

Optional Ingredients

The pouch including the prills, particles, and/or fibrous sheets can include optional ingredients that are known for use or otherwise useful in compositions, provided that such optional materials are compatible with the materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials. Further non-limiting examples of optional ingredients include encapsulated perfumes, such as by β-cyclodextrins, polymer microcapsules, starch encapsulated accords and combinations thereof.

In other examples, particles and/or agglomerated particles can be added to the internal volume of the pouch in addition to/or instead of the prills that contain anionic surfactant that are described herein. In some examples, the particles can be water-soluble matrix particles that contain a hydrophobic active agent as described in US Pub. Nos. 2020/0093710 and 2020/0093711, incorporated by reference. The hydrophobic active agent may be selected from the group consisting of: perfumes, essential oils, oils, vitamin oils, vegetable oils, silicones, shea butter, cocoa butter, petrolatum, tea tree oil, medium-chain ($C_6$-$C_{12}$)triglycerides, and mixtures thereof.

Making the Fibrous Structure

The fibrous elements, forming the fibrous sheet(s), of the present invention may be made by any suitable process. A non-limiting example of a suitable process for making the fibrous elements is described below.

Figure 3:
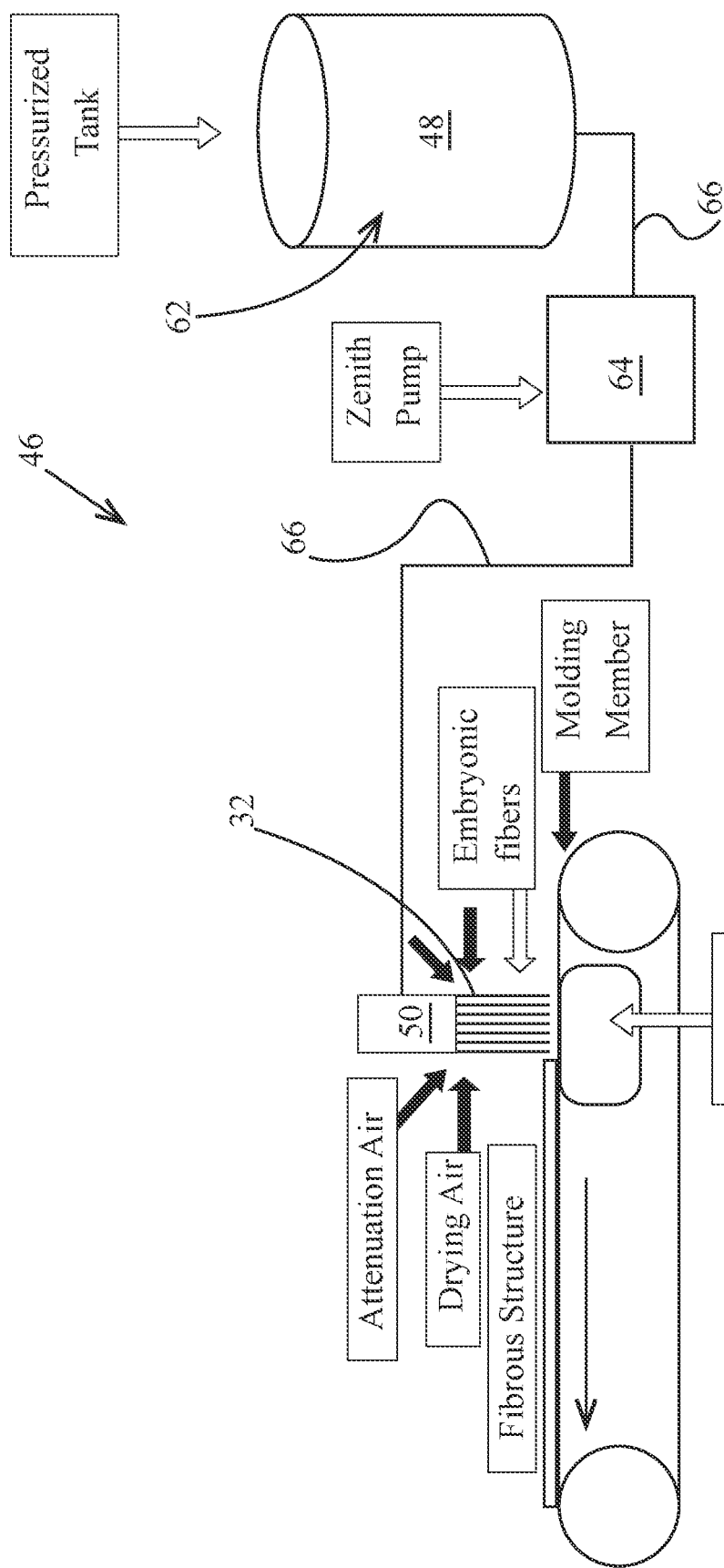
FIG. 3 is a schematic representation of an example of a process for making fibrous elements of the present invention.
Figure 4:
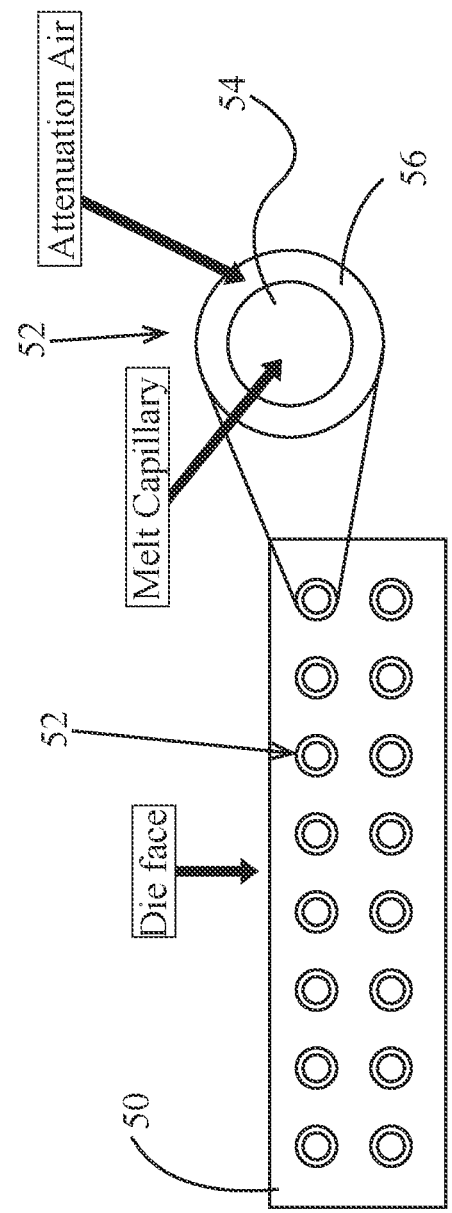
FIG. 4 is a schematic representation of an example of a die with a magnified view used in the process of FIG. 3.

In one example, as shown in FIGS. 3 and 4 a method 46 for making a fibrous element 32 according to the present invention comprises the steps of:

a. providing a filament-forming composition 48 comprising one or polymeric structurants, and optionally one or more other ingredients, wherein the filament-forming composition can comprise a pH of greater than about 5.5, alternatively greater than about 5.8, alternatively greater than 6.0; and b. spinning the filament-forming composition 48, such as via a spinning die 50, into one or more fibrous elements 32, such as filaments, comprising the one or more polymeric structurants and optionally, the one or more other ingredients. The one or more other ingredients may be releasable from the fibrous element when exposed to conditions of intended use.

As shown in FIG. 4, the spinning die 50 may comprise a plurality of fibrous element-forming holes 52 that include a melt capillary 54 encircled by a concentric attenuation fluid hole 56 through which a fluid, such as air, passes to facilitate attenuation of the filament-forming composition 48 into a fibrous element 32 as it exits the fibrous element-forming hole 52. It was found that if the filament forming composition had a pH of greater than about 5.5, better filaments can form after drying.

In one example, during the method for making fibrous elements, any volatile solvent, such as water, present in the filament-forming composition 48 is removed, such as by drying, as the fibrous element 32 is formed. In one example, greater than 30% and/or greater than 40% and/or greater than 50% and/or greater than 60% and/or greater than 70% of the weight of the filament-forming composition's volatile solvent, such as water, is removed during the spinning step, such as by drying the fibrous element being produced.

It was found that during the spinning step, the inventive examples in Table 5, below, can be sensitive to excessive heat exposure during the method for making fibrous elements. For example, if the fibrous elements are exposed to excessive heat for too long the fibrous elements can have active degradation and/or color change and/or odor change. However, the temperature needs to be high enough so the solvent can evaporate within an acceptable time period.

In one example, when the fibrous element exits the fibrous element-forming hole 52, they are collected on a belt above a vacuum source called the forming zone. The fibrous elements can remain on the forming zone for the following times and temperatures: from about 150° F. (65.6° C.) to about 160° F. (71.1° C.) for about 50 to about 60 seconds and/or from about 170° F. (65.6° C.) to about 180° F. (82.2° C.) for about 30 to about 40 seconds and/or from about 200° F. (93.3° C.) to about 215° F. (101.7° C.) for about 5 to about 20 seconds.

In one example, to enable the balance of solvent evaporation, dwell time, and heat exposure it is apparent that melt spinning temperature could be from about 70° F. to about 95° F. while enabling drying with heat such as about 340° F. (171.1° C.) to about 350° F. (176.7° C.) for about 50 to about 60 seconds or from about 390° F. (198.9° C.) to about 400° F. (204° C.) for about 30 to about 40 seconds or 415° F. (212.8° C.) to 470° F. (243.3° C.) for about 5 to about 20 seconds.

The filament-forming composition is spun into one or more fibrous elements and/or particles by any suitable spinning process, such as meltblowing, spunbonding, electro-spinning, and/or rotary spinning. In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt, such as a patterned belt to form a fibrous structure comprising the fibrous elements.

Non-Limiting Example for Making a Pouch

An example of a pouch of the present invention may be made as follows. The fibrous structure is bonded at discrete points to form the facing sheet and/or the backing sheet materials. The fibrous structure may not be bonded to another fibrous structure, film, or sheet. Instead, the fibrous structure is bonded separately to create bonding points on the outer surface of each sheet. During the bonding process the facing sheet may not be bound directly to the backing sheet at the bonding points. Non-limiting examples of bonding processes can include thermal bonding, pressure bonding, ultrasonic bonding, and combinations thereof.

The pouch can be made by cutting the facing and backing sheet materials to larger than the size of the pouch size intended to make. For example, if finished pouch size has a planar footprint of about 2 inches (5.08 cm)×2 inches (5.08 cm), then the facing and backing sheet materials are cut 5 inches (12.7 cm)×5 inches (12.7 cm). Next, lay both sheet materials on top of one another on the heating element of an impulse sealer (Impulse Sealer model TISH-300 from TEW Electric Heating Equipment CO., LTD, 7F, No. 140, Sec. 2, Nan Kang Road, Taipei, Taiwan). The position of the sheets on the heating element should be where a side closure seal is to be created. Close the sealer arm for 1 second to seal the two layers together. In a similar way, seal two more sides to create two additional side closure seals. With the three sides sealed, the two sheet materials form a pocket with a facing sheet and a backing sheet.

Next, add the appropriate amount of prills into the pocket and then seal the last side to create the last side closure seal. A pouch is now formed. Depending on thickness of the sheeting materials, heating temperature and heating time might have to be adjusted to realize a desirable seam. If the temperature is too low or the heating time is not long enough, the film wall material may not sufficiently melt and the two sheets come apart easily; if the temperature is too high or the heating time is too long, pin holes may form at the sealed edge. One should adjust the sealing equipment conditions to the sheets to melt and form a seal but not introduce negatives such as pin holes on the seal edge. Once the sealed pouch is formed, a scissor is used to trim off the excess material and leave a 1-2 mm edge on the outside of the seamed pouch.

In some examples, the pouch can be made with one fibrous sheet that is bonded and then folded in half, forming the bottom of the pouch, sealed on the sides, filled with prills, and then sealed across the top. When made with one fibrous sheet, the finished pouch has a facing sheet and a backing sheet.

EXAMPLES

The following are non-limiting examples of the compositions described herein. It will be appreciated that other modifications of the present invention within the skill of those in the art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The prills in Table 1 and Table 2, below, were made or could be made by any conventional prilling method. The prills were ground and sieved to 250 μm or less.

In Table 1, the conditioner prills in Examples 1 and 2 were made and the conditioner prills in Examples 3-10 could be made. The prills in Table 1 can provide a conditioning benefit and contained/could contain a cationic surfactant (behentrimonium methosulfate, behentrimonium chloride, searamidopropyl dimethylamine, and/or behenamidopropyl dimethylamine) and a fatty alcohol (stearyl alcohol and 1-hexadecanol).

The prills in Table 1 are expected to be consumer acceptable. Some consumers may prefer a solid conditioning product that contains behentrimonium chloride as the primary or sole cationic surfactant because products with these surfactants can swell faster and produce a conditioner with a thicker consistency, as compared to other similar cationic surfactants.

TABLE 1

Conditioner Prills

| Raw Material | Ex 1 | Ex 2 | Ex 3 | Ex 4 | Ex 5 | Ex 6 | Ex 7 | Ex 8 | Ex 9 | Ex 10 | Ex 11 |
|---|---|---|---|---|---|---|---|---|---|---|---|
| Behentrimonium Methosulfate[1] | 32.6 | 0 | 0 | 0 | 15 | 0 | 0 | 0 | 25 | 0 | 32.6 |
| Behentrimonium Chloride[2] | 0 | 32.6 | 0 | 0 | 0 | 15 | 0 | 0 | 0 | 25 | 0 |
| Stearamidopropyl Dimethylamine[3] | 0 | 0 | 32.6 | 0 | 0 | 0 | 15 | 0 | 0 | 0 | 0 |
| Behenamidopropyl Dimethylamine[4] | 0 | 0 | 0 | 32.6 | 0 | 0 | 0 | 15 | 0 | 0 | 0 |
| Stearyl Alcohol | 45.0 | 45.0 | 41.0 | 41.0 | 56.7 | 56.7 | 54.2 | 54.2 | 50.6 | 50.6 | 40.0 |
| 1-Hexadecanol | 22.4 | 22.4 | 20.4 | 20.4 | 28.3 | 28.3 | 30.0 | 30.0 | 24.4 | 24.4 | 20.4 |
| Lactic Acid[5] | 0 | 0 | 6 | 6 | 0 | 0 | 3.8 | 3.8 | 0 | 0 | 0 |
| Perfume | 0 | 0 | 0 | 0 | 0 | 0 | 0 | 0 | 0 | 0 | 7 |

[1]Behentrimonium Methosulfate - IPA from Croda ®
[2]Genamin ® KDMP from Clariant ®
[3]Stearamidopropyl Dimethylamine from Croda ®
[4]Behenamidopropyl Dimethylamine from Croda ™
[5]Lactic Acid from Sigma Aldrich ® W261106-1KG-K Table 2, below, includes examples of prills that could be made according to the invention described herein. The prills in these examples could contain cationic conditioning surfactants and an zinc pyrithione (ZPT) antidandruff active. To add other antidandruff actives, such Piroctone olamine (commercially available as Octopirox®), it could be added as a separate particle in addition to or instead of ZPT.

TABLE 2

Conditioner Prills with Zinc Pyrithione Antidandruff Active

| Raw Material | Ex 11 | Ex 12 | Ex 13 | Ex 14 | Ex 15 | Ex 16 | Ex 17 | Ex 18 | Ex 19 | Ex 20 |
|---|---|---|---|---|---|---|---|---|---|---|
| Behentrimonium Methosulfate [1] | 32.6 | 0 | 0 | 0 | 25 | 0 | 0 | 0 | 0 | 0 |
| Behentrimonium Chloride[2] | 0 | 32.6 | 0 | 0 | 0 | 25 | 32.6 | 32.6 | 32.6 | 32.6 |
| Stearamidopropyl Dimethylamine[3] | 0 | 0 | 32.6 | 0 | 0 | 0 | 0 | 0 | 0 | 0 |
| Behenamidopropyl Dimethylamine[4] | 0 | 0 | 0 | 32.6 | 0 | 0 | 0 | 0 | 0 | 0 |
| Stearyl Alcohol | 43.4 | 44.2 | 38.2 | 39 | 49.0 | 49.0 | 44.9 | 44.9 | 44.2 | 44.8 |
| 1-Hexadecanol | 22.0 | 22.2 | 19.2 | 19.4 | 24.0 | 25.0 | 22.3 | 22.3 | 22.2 | 22.6 |
| Lactic Acid[5] | 0 | 0 | 8 | 8 | 0 | 0 | 0 | 0 | 0 | 0 |
| Zinc Pyrithione | 2 | 0 | 2 | 0 | 2 | 0 | 0 | 0 | 0 | 0 |
| Piroctone olamine | 0 | 1 | 0 | 1 | 0 | 1 | 0 | 0 | 0 | 0 |
| Disodium EDTA | 0 | 0 | 0 | 0 | 0 | 0 | 0.2 | 0 | 0 | 0 |
| Sodium Chloride | 0 | 0 | 0 | 0 | 0 | 0 | 0 | 0.2 | 0 | 0 |
| Histadine | 0 | 0 | 0 | 0 | 0 | 0 | 0 | 0 | 1 | 0 |

[1] Behentrimonium Methosulfate - IPA from Croda ®
[2] Genamin ® KDMP from Clariant ®
[3] Stearamidopropyl Dimethylamine from Croda ®
[4] Behenamidopropyl Dimethylamine from Croda ™
[5] Lactic Acid from Sigma Aldrich ® W261106-1KG-K
6. Amodimethicone from Momentive ® Performance Materials The particles in Table 3 and Table 4 can be made in any suitable method including the method disclosed in US Pub. No. 2020/0093710, incorporated by reference.

TABLE 3

Matrix Particles with Perfume

| | Ex. A | Ex. B | Ex. C | Ex. D | Ex. E | Ex. F |
|---|---|---|---|---|---|---|
| 31523 Corn Starch/ Maltodextrin Crosspolymer[1] | 57 | 57 | 57 | 0 | 0 | 0 |
| HiCap Starch[2] | 0 | 0 | 0 | 60 | 60 | 60 |
| Perfume #1 | 43 | 0 | 0 | 40 | 0 | 0 |
| Perfume #2 | 0 | 43 | 0 | 0 | 40 | 0 |
| Perfume #3 | 0 | 0 | 43 | 0 | 0 | 40 |

[1] Envicap ™ Crosslinked Starch from TruCapSol ™
[2] Hi-Cap ® 100 from Ingredion ™

TABLE 4

Particles with Silicone

| | Ex. A | Ex. B | Ex. C | Ex. D | Ex. E | Ex. F |
|---|---|---|---|---|---|---|
| Purity Gum 59 Starch[1] | 58 | 0 | 0 | 0 | 0 | 29 |
| Hi-Cap Starch[1] | 0 | 58 | 0 | 0 | 0 | 29 |
| PVOH 505[2] | 0 | 0 | 58 | 0 | 20 | |
| PVOH 403[2] | | | | 58 | 38 | |
| Amodimethicone | 32 | 32 | 32 | 32 | 32 | 32 |
| Emulsifiers | 10 | 10 | 10 | 10 | 10 | 10 |

[1] Ingredion ®
[2] Kuraray ®

In Table 5, below, Examples B, C, E, and F were made by the method for making fibrous the structure, described herein. Examples A, D, G, H, and I could be made using the same method.

TABLE 5

Fibrous Starch Sheet

| | Ex. A | Ex. B | Ex. C | Ex. D | Ex. E | Ex. F | Ex. G | Ex. H | Ex. I |
|---|---|---|---|---|---|---|---|---|---|
| Purity Gum 59 Starch[1] | 100 | 0 | 0 | 90 | 0 | 0 | 0 | 0 | 0 |
| Purity Gum Ultra Starch[1] | 0 | 100 | 0 | 0 | 90 | 0 | 0 | 0 | 0 |
| Purity Gum BE Starch[1] | 0 | 0 | 100 | 0 | 0 | 90 | 0 | 0 | 0 |
| Glycerol | 0 | 0 | 0 | 10 | 10 | 10 | 0 | 0 | 0 |
| PVOH 403 [2] | 0 | 0 | 0 | 0 | 0 | 0 | 98 | 64 | 90 |
| PVOH 505 [2] | 0 | 0 | 0 | 0 | 0 | 0 | 0 | 34 | 0 |
| PVOH 420H [2] | 0 | 0 | 0 | 0 | 0 | 0 | 0 | 0 | 10 |
| Histadine | 0 | 0 | 0 | 0 | 0 | 0 | 2 | 2 | 1 |

[1] Ingredion ®
[2] Kuraray ®

The fibrous starch sheet of Table 5, can be made into a pouch as described herein. After sealing three sides of the fibrous starch sheet, approximately 2 grams of prills and particles from Table 1, Table 2, Table 3, and/or Table 4 can be added to the internal volume and then the pouch can be sealed to form a water-soluble pouch. The water-soluble pouch in these examples can be a rinse-off hair conditioner that can also include perfumes, silicones, and/or anti-dandruff actives.

TEST METHODS

Unless otherwise specified, all tests described herein including those described under the Definitions section and the following test methods are conducted on samples that have been conditioned in a conditioned room at a temperature of 22° C.±2° C. and a relative humidity of 42%±4% for a minimum of 2 hours prior to the test. The samples tested are "usable units." "Usable units" as used herein means water-soluble pouches with our without prills, sheets, flats from roll stock, pre-converted flats, and/or single or multi-ply products. All tests are conducted under the same environmental conditions and in such conditioned room. Do not test samples that have defects such as wrinkles, tears, holes, and like. Samples conditioned as described herein are considered dry samples (such as "dry filaments") for testing purposes. All instruments are calibrated according to manufacturer's specifications.

Basis Weight

The Basis Weight of the personal care article and/or the porous dissolvable solid substrate is calculated as the weight of the personal care article and/or the porous dissolvable solid substrate per area of the selected personal care article and/or the porous dissolvable solid substrate (grams/m$^2$). The area is calculated as the projected area onto a flat surface perpendicular to the outer edges of the personal care article and/or the porous dissolvable solid substrate. For a flat object, the area is thus computed based on the area enclosed within the outer perimeter of the sample. For a spherical object, the area is thus computed based on the average diameter as $3.14 \times (diameter/2)^2$. For a cylindrical object, the area is thus computed based on the average diameter and average length as diameter×length. For an irregularly shaped three-dimensional object, the area is computed based on the side with the largest outer dimensions projected onto a flat surface oriented perpendicularly to this side.

Diameter Test Method

The diameter of a discrete fibrous element or a fibrous element within a fibrous article is determined by using a Scanning Electron Microscope (SEM) or an Optical Microscope and an image analysis software. A magnification of 200 to 10,000 times is chosen such that the fibrous elements are suitably enlarged for measurement. When using the SEM, the samples are sputtered with gold or a palladium compound to avoid electric charging and vibrations of the fibrous element in the electron beam. A manual procedure for determining the fibrous element diameters is used from the image (on monitor screen) taken with the SEM or the optical microscope. Using a mouse and a cursor tool, the edge of a randomly selected fibrous element is sought and then measured across its width (i.e., perpendicular to fibrous element direction at that point) to the other edge of the fibrous element. A scaled and calibrated image analysis tool provides the scaling to get actual reading in μm. For fibrous elements within a fibrous article, several fibrous elements are randomly selected across the sample of the fibrous article using the SEM or the optical microscope. At least two portions of the fibrous article are cut and tested in this manner Altogether at least 100 such measurements are made and then all data are recorded for statistical analysis. The recorded data are used to calculate average (mean) of the fibrous element diameters, standard deviation of the fibrous element diameters, and median of the fibrous element diameters.

Another useful statistic is the calculation of the amount of the population of fibrous elements that is below a certain upper limit. To determine this statistic, the software is programmed to count how many results of the fibrous element diameters are below an upper limit and that count (divided by total number of data and multiplied by 100%) is reported in percent as percent below the upper limit, such as percent below 1 micrometer diameter or %-submicron, for example. We denote the measured diameter (in μm) of an individual circular fibrous element as di.

In the case that the fibrous elements have non-circular cross-sections, the measurement of the fibrous element diameter is determined as and set equal to the hydraulic diameter which is four times the cross-sectional area of the fibrous element divided by the perimeter of the cross-section of the fibrous element (outer perimeter in case of hollow fibrous elements). The number-average diameter, alternatively average diameter is calculated as:

$$d_{num} = \frac{\sum_{i=1}^{n} d_i}{n}$$

Fibrous Element Composition Test Method

In order to prepare fibrous elements for fibrous element composition measurement, the fibrous elements must be conditioned by removing any coating compositions and/or materials present on the external surfaces of the fibrous elements that are removable. An example of a method for doing so is washing the fibrous elements 3 times with a suitable solvent that will remove the external coating while leaving the fibrous elements unaltered. The fibrous elements are then air dried at 23° C.±1.0° C. until the fibrous elements comprise less than 10% moisture. A chemical analysis of the conditioned fibrous elements is then completed to determine the compositional make-up of the fibrous elements with respect to the filament-forming materials and the active agents and the level of the filament-forming materials and active agents present in the fibrous elements.

The compositional make-up of the fibrous elements with respect to the filament-forming material and the active agents can also be determined by completing a cross-section analysis using TOF-SIMs or SEM. Still another method for determining compositional make-up of the fibrous elements uses a fluorescent dye as a marker. In addition, as always, a manufacturer of fibrous elements should know the compositions of their fibrous elements.

Hand Dissolution Method

Materials Needed:

Fibrous articles to be tested: 3-5 fibrous articles (finished product samples) are tested so that an average of the number of strokes for each if the individual fibrous article samples is calculated and recorded as the Average Hand Dissolution value for the fibrous article. For this method, the entire consumer saleable or consumer use fibrous article is tested. If the entire consumer saleable or consumer use fibrous article has a footprint greater than 50 cm$^2$, then first cut the fibrous article to have a footprint of 50 cm$^2$.

Nitrile Gloves
10 cc syringe
Plastic Weigh boat (~3 in×3 in)
100 mL Glass beaker
Water (City of Cincinnati Water or equivalent having the following properties: Total Hardness=155 mg/L as $CaCO_2$; Calcium content=33.2 mg/L; Magnesium content=17.5 mg/L; Phosphate content=0.0462 mg/L). Water used is water 7 grains per gallon (gpg) hardness and 40° C.+/−5° C.
Protocol:
Add 80 mL of water to glass beaker.
Heat water in beaker until water is at a temperature of 40° C.+/−5° C.
Transfer 15 mL of the water from the beaker into the weigh boat via the syringe.
Within 10 seconds of transferring the water to the weigh boat, place fibrous article sample in palm of gloved hand (hand in cupped position in non-dominant hand to hold fibrous article sample).
Using dominant hand, add water quickly from the weigh boat to the fibrous article sample and allow to immediately wet for a period of 5-10 seconds.
Rub with opposite dominant hand (also gloved) in 2 rapid circular strokes.
Visually examine the fibrous article sample in hand after the 2 strokes. If fibrous article sample is completely dissolved, record number of strokes=2 Dissolution Strokes. If not completely dissolved, rub remaining fibrous article sample for 2 more circular strokes (4 total) and observe degree of dissolution. If the fibrous article sample contains no solid pieces after the 2 additional strokes, record number of strokes=4 Dissolution Strokes. If after the 4 strokes total, the fibrous article sample still contains solid pieces of un-dissolved fibrous article sample, continue rubbing remaining fibrous article sample in additional 2 circular strokes and check if there are any remaining solid pieces of fibrous article sample after each additional 2 strokes until fibrous article sample is completely dissolved or until reaching a total of 30 strokes, whichever comes first. Record the total number of strokes. Record 30 Dissolution Strokes even if solid fibrous article sample pieces remain after the maximum of 30 strokes.
Repeat this process for each of the additional 4 fibrous article samples.
Calculate the arithmetic mean of the recorded values of Dissolution Strokes for the 5 individual fibrous article samples and record as the Average Hand Dissolution Value for the fibrous article. The Average Hand Dissolution Value is reported to the nearest single Dissolution Stroke unit.

Median Particle Size Test Method

This test method must be used to determine median particle size.

The median particle size test is conducted to determine the median particle size of the seed material using ASTM D 502-89, "Standard Test Method for Particle Size of Soaps and Other Detergents", approved May 26, 1989, with a further specification for sieve sizes used in the analysis. Following section 7, "Procedure using machine-sieving method," a nest of clean dry sieves containing U.S. Standard (ASTM E 11) sieves #8 (2360 urn), #12 (1700 urn), #16 (1180 urn), #20 (850 urn), #30 (600 urn), #40 (425 urn), #50 (300 urn), #70 (212 urn), #100 (150 μm) is required. The prescribed Machine-Sieving Method is used with the above sieve nest. The seed material is used as the sample. A suitable sieve-shaking machine can be obtained from W.S. Tyler Company of Mentor, Ohio, U.S.A.

The data are plotted on a semi-log plot with the micron size opening of each sieve plotted against the logarithmic abscissa and the cumulative mass percent (Q3) plotted against the linear ordinate. An example of the above data representation is given in ISO 9276-1:1998, "Representation of results of particle size analysis—Part 1: Graphical Representation", Figure A.4. The seed material median particle size (D50), for the purpose of this invention, is defined as the abscissa value at the point where the cumulative mass percent is equal to 50 percent, and is calculated by a straight line interpolation between the data points directly above (a50) and below (b50) the 50% value using the following equation:

$$D_{50}=10[\text{Log }(D_a 50)-(\text{Log }(D_{a50})-\text{Log }(D_{b50}))*(Qa5o-50\%)/(Q_{a50}-Qbso)]$$

where $Q_a$so and $Q_b$so are the cumulative mass percentile values of the data immediately above and below the 50th percentile, respectively; and $D_a$so and D so are the micron sieve size values corresponding to these data.

In the event that the 50th percentile value falls below the finest sieve size (150 um) or above the coarsest sieve size (2360 um), then additional sieves must be added to the nest following a geometric progression of not greater than 1.5, until the median falls between two measured sieve sizes.

The Distribution Span of the Seed Material is a measure of the breadth of the seed size distribution about the median. It is calculated according to the following:

$$\text{Span}=(D_{84}/D_{50}+D_{50}/D_{16})/2$$

Where D50 is the median particle size and $D_{84}$ and $D]_6$ are the particle sizes at the sixteenth and eighty-fourth percentiles on the cumulative mass percent retained plot, respectively. In the event that the $D]_6$ value falls below the finest sieve size (150 um), then the span is calculated according to the following:

$$\text{Span}=(D_{84}/D_{50}).$$

In the event that the $D_{84}$ value falls above the coarsest sieve size (2360 um), then the span is calculated according to the following:

$$\text{Span}=(D_{50}/D_{16}).$$

In the event that the $D]_6$ value falls below the finest sieve size (150 um) and the $D_{84}$ value falls above the coarsest sieve size (2360 um), then the distribution span is taken to be a maximum value of 5.7.

Melting Point Test Method
Equipment
  Heating block fitted with receptacles sized for scintillation vials
  Scintillation vial
Procedure
  Place ~3 g of material in a scintillation vial—approximately enough material to form a single layer of prills at the bottom of the vial
  Place vial in a heat block that is heated to 40° C.
  Allow vial to heat in block for 15 minutes initially to ensure sample has been heated to block temperature
  Increase temperature gradually in 5° C. increments, inspecting prills in vial occasionally for signs of melting. Vial should rest at a temperature for ~15 min to ensure the temperature of the sample has equilibrated
  The temperature at which the prills begin to lose their original form and a pool begins to form in the bottom of the vial is the recorded as the melting point Combinations A. A water-soluble pouch for hair care comprising:
   a. a water-soluble pouch defining an internal volume comprising:
      i. a water-soluble fibrous facing sheet comprising a perimeter, an outer surface, and an inner surface; and
      ii. a water-soluble fibrous backing sheet comprising a perimeter, an outer surface, and an inner surface;
         wherein the facing sheet and the backing sheet are sealed along at least a portion of the perimeters to form a pouch defining an internal volume;
         wherein the fibrous structure comprises a plurality of two or more fibrous elements that are inter-entangled or otherwise associated with one another;
         wherein the fibrous elements comprise a polymeric structurant that is thermally sealable without the addition of an adhesive or other composition;
         wherein the outer surfaces and/or the inner surfaces of the facing and backing sheets comprise a plurality of bonding points;
   b. a plurality of prills within the internal volume comprising:
      i. from 1% to 60%, preferably from 5% to 50%, more preferably from 10% to 40%, most preferably from 13% to 35%, by weight of the prills, of a cationic surfactant selected from behentrimonium methosulfate, brassicamidopropyl dimethylamine, behentrimonium chloride, stearamidopropyl dimethylamine, behenamidopropyl dimethylamine, and combinations thereof;
      ii. from 10% to 90%, preferably from 28% to 90%, preferably from 35% to 87%, and more preferably from 38% to 85% by weight of the prills, of a fatty alcohol;
         wherein the prills comprise a melting point of greater than 40° C., preferably greater than 45° C., more preferably greater than 50° C., according to the Melting Point Test Method described herein.

B. The pouch according to Paragraph A, wherein the prills comprise a length of less than 750 μm, preferably less than 500 μm, more preferably less than 300 μm.

C. The pouch according to Paragraphs A-B, wherein the facing sheet and the backing sheet are substantially free of apertures, preferably free of apertures.

D. The pouch according to Paragraphs A-C, wherein the water-soluble fibrous facing sheet and backing sheet are substantially free of a cationic surfactant, preferably free of a cationic surfactant.

E. The pouch according to Paragraphs A-D, wherein the pouch is substantially free of an acyl glucamide, preferably free of an acyl glucamide.

F. The pouch according to Paragraphs A-E, wherein the polymeric structurant is selected from starch, cellulose, hemicellulose, and mixtures and derivatives thereof.

G. The pouch according to Paragraphs A-F, wherein a single fibrous sheet comprises the facing sheet and the backing sheet and at least an edge of the pouch is formed by folding the fibrous sheet.

H. The pouch according to Paragraphs A-G, wherein the facing sheet and the backing sheet are separate fibrous sheets and the seal permanently joins the facing sheet to the backing sheet along substantially the entire perimeter.

I. The pouch according to Paragraphs A-H, wherein the fatty alcohol is selected from cetyl alcohol, stearyl alcohol, behenyl alcohol, and mixtures thereof.

J. The pouch according to Paragraphs A-I, wherein the prills comprise a molar ratio of cationic surfactant to fatty alcohol from 1:8 to 4:5, preferably from 1:7 to 2:3, more preferably from 1:6 to 3:5, most preferably from 1:5 to 1:3.

K. The pouch according to Paragraphs A-J, wherein the weight ratio of prills to the facing and backing sheets is from 2:1 to 8:1, preferably from 3:1 to 6:1, and more preferably from 4:1 to 5:1.

L. The pouch according to Paragraphs A-K, wherein the pouch comprises a hand dissolution of less than 15 strokes, preferably less than 12 strokes, more preferably less than 10 strokes according to the Hand Dissolution Method, described herein.

M. The pouch according to Paragraphs A-L, wherein the pouch comprises a basis weight of less than 150 grams/m$^2$, preferably less than 125 grams/m$^2$, more preferably less than 100 grams/m$^2$, and most preferably less than 80 grams/m$^2$, according to the Basis Weight Test Method, described herein.

N. The pouch according to Paragraphs A-M, wherein the fatty alcohol comprises cetyl alcohol and stearyl alcohol and the ratio of cetyl alcohol to stearyl alcohol is from 1:4 to 4:1.

O. The pouch according to Paragraphs A-N, wherein the prills are free flowing.

P. The pouch according to Paragraphs A-O, wherein the seal comprises a thermal seal.

Q. A water-soluble pouch of for hair care comprising:
   a. a water-soluble pouch defining an internal volume comprising:
      i. a water-soluble fibrous facing sheet comprising a perimeter, an outer surface, and an inner surface; and
      ii. a water-soluble fibrous backing sheet comprising a perimeter, an outer surface, and an inner surface;
         wherein the facing sheet and the backing sheet comprise a thermal seal joining the facing sheet to the backing sheet along at least a portion of the perimeters;
         wherein the fibrous structure comprises a plurality of two or more fibrous elements that are inter-entangled or otherwise associated with one another;
         wherein the fibrous elements comprise a polymeric structurant that is thermally sealable without the addition of an adhesive or other composition;
         wherein the outer surfaces and/or the inner surfaces of the facing and backing sheets comprise a plurality of bonding points;
   b. a plurality of prills within the internal volume comprising:
      i. from 1% to 60%, preferably from 5% to 50%, more preferably from 10% to 40%, most preferably from 13% to 35%, by weight of the prills, of an anionic surfactant;
      ii. optionally a zwitterionic co-surfactant selected from of cocoamiodpropyl betaines, lauramidopropyl betaine, and combinations thereof;
         wherein the prills comprise a melting point of greater than 45° C., preferably greater than 45° C., more preferably greater than 50° C., according to the Melting Point Test Method described herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A water-soluble article for hair care comprising:
   a. a water-soluble pouch defining an internal volume comprising:
      i. a water-soluble, non-continuous, fibrous facing sheet comprising a perimeter, an outer surface, and an inner surface; and
      ii. a water-soluble, non-continuous, fibrous backing sheet comprising a perimeter, an outer surface, and an inner surface;
      wherein the facing sheet and the backing sheet comprise a thermal seal joining the facing sheet to the backing sheet along at least a portion of the perimeters to form the internal volume;
      wherein the fibrous facing sheet and the fibrous backing sheet comprise a plurality of fibrous elements that are inter-entangled or otherwise associated with one another;
      wherein the plurality of fibrous elements comprise a polymeric structurant that is thermally sealable without the addition of an adhesive or other composition; and
      wherein the outer surfaces and/or the inner surfaces of the facing and backing sheets comprise from about 5 to about 25 bonding points per $cm^2$ distributed across the facing sheet and/or backing sheet; wherein the bonding points extend completely or partially through the facing and/or backing sheet and the facing sheet is not bound directly to the backing sheet at the bonding points;
      wherein the water-soluble fibrous facing sheet and backing sheet are substantially free of a surfactant; and
   b. a plurality of prills within the internal volume comprising:
      i. from about 1% to about 60%, by weight of the prills, of a cationic surfactant chosen from behentrimonium methosulfate, brassicamidopropyl dimethylamine, behentrimonium chloride, stearamidopropyl dimethylamine, and/or behenamidopropyl dimethylamine;
      ii. from about 10% to about 90%, by weight of the prills, of a fatty alcohol;
   wherein the prills comprise a melting point of greater than 45° C.

2. The article of claim 1, wherein the melting point of the prills is greater than 50° C.

3. The article of claim 1, wherein the prills comprise a length of less than 300 µm.

4. The article of claim 1, wherein the facing sheet and the backing sheet are substantially free of apertures.

5. The article of claim 1, wherein the water-soluble fibrous facing sheet and backing sheet are substantially free of a fatty alcohol.

6. The article of claim 1, wherein the water-soluble pouch is substantially free of an acyl glucamide.

7. The article of claim 1, wherein the polymeric structurant is chosen from starch, cellulose, hemicellulose, or mixtures thereof.

8. The article of claim 1, wherein a fibrous sheet comprises the facing sheet and the backing sheet and at least an edge of the pouch is formed by folding the fibrous sheet.

9. The article of claim 1, wherein the facing sheet and the backing sheet are separate fibrous sheets and the thermal seal permanently joins the facing sheet to the backing sheet along substantially the entire perimeter.

10. The article of claim 1, wherein the fatty alcohol is chosen from cetyl alcohol, stearyl alcohol, behenyl alcohol, or mixtures thereof.

11. The article of claim 1, wherein the prills comprise a molar ratio of cationic surfactant to fatty alcohol from about 1:6 to about 3:5.

12. The article of claim 1, comprising a weight ratio of prills to the facing and backing sheets of from about 2:1 to about 8:1.

13. The article of claim 1 wherein the pouch comprises a hand dissolution of less than 15 strokes according to the Hand Dissolution Method.

14. The article of claim 1, wherein the pouch comprises a basis weight of less than 150 grams/$m^2$.

15. A water-soluble article for hair care comprising:
   a. a water-soluble fibrous pouch defining an internal volume;
      i. a water-soluble, non-continuous, fibrous facing sheet comprising a perimeter, an outer surface, and an inner surface; and
      ii. a water-soluble, non-continuous, fibrous backing sheet comprising a perimeter, an outer surface, and an inner surface;
      wherein the facing sheet and the backing sheet are sealed along the perimeters to form a pouch defining an internal volume;
      wherein the fibrous facing sheet and fibrous backing sheet comprise a plurality of fibrous elements that are inter-entangled or otherwise associated with one another;
      wherein the plurality of fibrous elements comprise a polymeric structurant chosen from starch, cellulose, hemicellulose, polyvinyl alcohol, or mixtures thereof;
      wherein the facing sheet and the backing sheet comprise a seal permanently joining the facing sheet to the backing sheet along at least a portion of the perimeters;
      wherein the facing sheet and the backing sheet are substantially free of apertures;
      wherein the water-soluble fibrous facing sheet and backing sheet are free of a surfactant and fatty alcohol; and
   b. a plurality of prills within the internal volume comprising:
      i. from about 1% to about 60%, by weight of the prills, of a cationic surfactant chosen from behentrimonium methosulfate, brassicamidopropyl dimethylamine, behentrimonium chloride, stearamidopropyl dimethylamine, and/or behenamidopropyl dimethylamine;

ii. from about 10% to about 90%, by weight of the prills, of a fatty alcohol;

wherein the prills dissolve to form a gel network;

wherein the pouch comprises a melting point of greater than 45° C.; and wherein the internal volume is adapted to contain about 0.5 to about 5 grams of the prills.

16. The article of claim 15, wherein the fatty alcohol comprises cetyl alcohol and stearyl alcohol and the ratio of cetyl alcohol to stearyl alcohol is from about 1:4 to about 4:1.

17. The article of claim 15, wherein the prills are free flowing.

18. A water-soluble article for hair care comprising:

a. a water-soluble pouch defining an internal volume comprising:

i. a water-soluble fibrous facing sheet comprising a perimeter, an outer surface, and an inner surface; and ii. a water-soluble fibrous backing sheet comprising a perimeter, an outer surface, and an inner surface;

wherein the facing sheet and the backing sheet comprise a thermal seal joining the facing sheet to the backing sheet along at least a portion of the perimeters;

wherein the fibrous facing sheet and the fibrous backing sheet comprise a plurality of fibrous elements that are inter-entangled or otherwise associated with one another;

wherein the plurality of fibrous elements comprise a polymeric structurant that is thermally sealable without the addition of an adhesive or other composition;

wherein the outer surfaces and/or the inner surfaces of the facing and backing sheets comprise a plurality of bonding points;

b. a plurality of prills within the internal volume comprising:

i. from about 1% to about 60%, by weight of the prills, of an anionic surfactant;

ii. optionally a zwitterionic co-surfactant chosen from cocoamiodpropyl betaines, lauramidopropyl betaine, or mixtures thereof;

wherein the prills comprise a melting point of greater than 45° C.

* * * * *